(12) United States Patent
Kinders et al.

(10) Patent No.: US 6,221,621 B1
(45) Date of Patent: Apr. 24, 2001

(54) METHODS OF SCREENING FOR COLORECTAL CANCERS IN WHICH A COMPLEMENT FACTOR I OR RELATED PROTEIN IS ASSOCIATED

(75) Inventors: Robert J. Kinders, Woodinville; David L. Enfield, Bothell; G. Michael Hass, Issaquah, all of WA (US)

(73) Assignee: BARD Diagnostic Sciences, Inc., Redmond, WA (US)

( * ) Notice: Subject to any disclaimer, the term of this patent is extended or adjusted under 35 U.S.C. 154(b) by 0 days.

(21) Appl. No.: 09/067,400

(22) Filed: Mar. 5, 1998

Related U.S. Application Data

(60) Provisional application No. 60/038,615, filed on Mar. 6, 1997.

(51) Int. Cl.[7] .............................. C12Q 1/68; C12Q 1/37; G01N 33/53; G01N 33/573; C12P 19/34; C12N 91/50
(52) U.S. Cl. ..................... 435/7.23; 435/6; 435/7.1; 435/7.4; 435/91.2; 435/219; 436/821
(58) Field of Search .................. 435/6, 7.1, 91.2, 435/7.4, 219, 7.23; 436/821

(56) References Cited

U.S. PATENT DOCUMENTS 4,342,566  8/1982  Theofilopoulos et al. .

FOREIGN PATENT DOCUMENTS

| 244 267 A2 | 11/1987 | (EP) . |
|---|---|---|
| 358 130 A2 | 3/1990 | (EP) . |
| 512 733 A2 | 11/1992 | (EP) . |
| 685 739 A1 | 12/1995 | (EP) . |
| WO 89/04174 | 5/1989 | (WO) . |
| WO 91/05047 | 4/1991 | (WO) . |
| WO 93/07888 | 4/1993 | (WO) . |
| WO 96/07738 | 3/1996 | (WO) . |

OTHER PUBLICATIONS

Goldberger et al. J. Biol. Chem. 262 (21):10065–71, 1987.*
Hirose et al, J. Biol. Chem. 267:5272–5278, 1992.*
Ngu et al., (V) The Protein Folding Problem nd Tertiary Structure Prediction, 1994, Merz et al., (ed) Birkhauser, Boston, MA pp. 4333 and 492–95.*
Paul William, Fundamental Immunology 4th Edition p. 1238 Lippincott Raven Philadelphia PA, 1999.*

* cited by examiner

*Primary Examiner*—David Saunders
*Assistant Examiner*—Amy Decloux
(74) *Attorney, Agent, or Firm*—Seed Intellectual Property Law Group PLLC

(57) ABSTRACT

Methods of screening for cancers or treating cancers or autoimmune disorders are disclosed. In an aspect of the present invention, the screening methods are based on the detection of complement C3 or C3 related protein, or a nucleic acid molecule encoding the same, found to be associated with the presence of cancer. Additional screening methods are based on the use of complement regulators Factor I or DAF, or complement receptors 1 or 3. Preferred embodiments to the methods include detection based on immunological properties, physical properties, enzymatic properties and combinations thereof, or detection of a nucleic acid molecule encoding antigen based on nucleic acid amplification.

4 Claims, 16 Drawing Sheets

METHODS OF SCREENING FOR
COLORECTAL CANCERS IN WHICH A
COMPLEMENT FACTOR I OR RELATED
PROTEIN IS ASSOCIATED

CROSS-REFERENCE TO RELATED
APPLICATION

This application claims priority from U.S. Provisional Application Ser. No. 60/038,615, filed Mar. 6, 1997, which application is incorporated by reference in its entirety.

TECHNICAL FIELD

The present invention is generally directed toward screening for (detecting or monitoring) cancers or treating cancers or autoimmune disorders in which complement C3 or a C3 related protein is associated, or cancers in which certain complement regulators or complement receptors or related proteins are associated. The invention is more particularly related to detecting complement C3 protein or a C3 related protein (or a nucleic acid molecule encoding such a protein) or a certain complement regulator or complement receptor protein or related protein (or a nucleic acid molecule encoding such a protein), or to modulating the amount or activity of such a protein.

BACKGROUND OF THE INVENTION

Although the present invention disclosed in this application has applicability to a number of different cancers and disorders, only the background of selected representative cancers and autoimmune diseases is described for illustrative purposes.

A. Renal Cell Cancer

The annual incidence of renal cell cancer in the U.S. is approximately 30,000 cases, and this disease accounts for about 2.5% of cancer deaths in men and 1.8% in women. Diagnosis of the disease is so difficult that it has been called "the internist's tumor." This is due to the subtle clinical symptoms of this nearly silent killer.

About 10% of patients presenting with renal cancer have the symptoms of pain, hematuria and a flank mass of tissue, which are evidence of far advanced disease. In most cases, the cancer is found during a diagnostic study to discover a cause for a vague set of symptoms in an unwell patient. Current diagnostic methods include intravenous pyelography, ultrasound, MRI, CT, radionuclide scanning and aspiration and biopsy of a cyst. All methods are limited in their ability to distinguish cancerous from normal tissue, but tend to be very good at identifying cysts. Due to the association of other urinary tract cancers with renal cancer, it is recommended practice to routinely perform a cystoscopy to search for cancers of the urinary tract when a diagnosis of renal cancer has been made (Cancer Manual, 9th ed., 1996, American Cancer Society, Massachusetts Division, Framingham, Mass., pp. 434–445).

B. Cervical Cancer

The annual incidence of cervical cancer in the U.S. is estimated at 15,700 cases for 1996. Although this disease is highly treatable, approximately 4,900 patients die annually.

Risk of cervical cancer among women is difficult to determine. Therefore, the American College of Obstetrics and Gynecology recommends that most women undergo an annual cytological diagnostic test for cervical cancer, the Pap test. The diagnostic performance of the Pap test is good (false negative rate 5%–30%, false positive rate <5%), but the test suffers from a significant percentage of equivocal results, which are referred to as atypia. It is then recommended that smears which are atypical or show evidence of inflammation be repeated after any current infection has been successfully treated. The frequency of atypical results not only increases test costs, but also increases the risk to the average patient, since the major difficulty with the use of the Pap test as a screening tool is patient compliance. Further diagnostic procedures, and there are many, are all invasive to varying degrees.

C. Bladder Cancer

Bladder cancer is the fifth most common cancer in the United States. The American Cancer Society estimated that in 1996 a total of 52,900 new cases would be detected and that there would be 11,700 deaths resulting from this disease. The incidence of bladder cancer increases with age. It is more common in men than in women by a ratio of approximately three to one and has been shown to be highly associated with smoking as well as exposure to certain dyes. The most common type of bladder cancer is transitional cell carcinoma (TCC), representing greater than 90% of all cases.

The most common presenting symptoms are hematuria, which is observed in approximately 80% of the cases, and dysuria. Although hematuria is more often related to non-malignant conditions, it is recommended that in the presence of such symptoms an evaluation for bladder cancer be completed. Once infection of the urinary tract has been eliminated as a possibility, a full evaluation is likely to include urine cytology, intravenous pyelography and cystoscopy. The possibility of a positive diagnosis by cytology (i.e., the identification of tumor cells in voided urine) increases with the grade of the tumor. In some cases cytological evaluation may be necessary to detect tumor in situ or tumors which are located in the upper end of the bladder. Careful cystoscopic examination, with multiple biopsies taken in areas in and around a suspected tumor, is considered to be the gold standard for diagnosis of bladder cancer. Intravenous pyelography may aid in accurately determining the stage of the tumor.

Following the initial procedures for evaluation, transurethral biopsy and resection are usually performed. These enable removal of the apparent lesion and provide information regarding the clinical stage and extent of invasion of the tumor. Such information aids in the selection of appropriate therapeutic approaches and of subsequent monitoring procedures. As recurrence of superficial tumors is common, occurring in 75% of the cases, usually within 12 months after treatment, monitoring is crucial for the long-term survival of the patient. Therefore, patients with superficial TCC are typically monitored every three months for the first two years and, if there has been no recurrence, every six months during the following year. Because cystoscopy is invasive and unpleasant and because the reliability of urine cytology is variable in detecting recurrence, there is a significant need for a reliable, non-invasive diagnostic method.

D. Colorectal Cancer

The annual rate of incidence of colorectal cancer has fallen significantly since 1970. However, the estimate of new cases in the U.S. for 1996 was still 133,500, with a corresponding projection of 54,900 deaths. Colorectal cancer is third in incidence for both men and women in the U.S.

The key to falling incidence has been the advent of early detection, which has been made possible by the use in the U.S. of screening protocols. Screening includes testing for the presence of occult blood in stool specimens (by use of a product such as Hemoccult®), digital rectal examination, and sigmoidoscopy. The latter two procedures must be performed in the clinician's office and are not capable of detecting disease in the lateral or ascending colon. Therefore, not only is the presence of cancer often missed, but the clinician is left to guess whether to utilize additional procedures in order to visualize the entire colon. Such procedures, which include direct visualization by colonoscopy or X-ray visualization after giving a barium enema, are invasive, expensive, and time consuming.

The procedure for screening recommended by the American Cancer Society is colonoscopy, in that it allows the removal of polyps and biopsy of suspicious lesions at the time of the procedure. The decision to proceed with colonoscopy is based on the positive result of an occult blood test, a procedure with a sensitivity of approximately 37% and a specificity of approximately 97%.

The American Cancer Society recommends, for general screening, an annual digital rectal exam for all individuals beginning at age 40. At age 50, the Society further recommends initiation of an annual series of three double tests for occult blood by the guaiac method. Finally, the Society recommends that two initial sigmoidoscopies be performed one year apart, and that, if both are negative, further visualization by sigmoidoscopy be repeated every three to five years.

Patients diagnosed with colon cancer are often monitored with one or more blood tests for circulating tumor associated antigens, such as CEA or CA72-4 4. However, these markers are not capable of detecting early stage disease (A or B1 by the Dukes staging system), which can be readily treated, and are, therefore, not suitable for screening of the general population.

Accordingly, there is a need in the art for a non-invasive diagnostic method with reliability in detecting occurrence or recurrence of certain cancers. The present invention fulfills this need and further provides other related advantages.

E. Autoimmune Diseases

Autoimmune diseases are complex and have diverse mechanisms and pathologies. For clarity, diseases that are known to be mediated by production of specific antibodies to self-antigens, with the result being the destruction of host tissue, are described.

Antibodies to basement membranes of lung and kidney glomeruli are produced by individuals with Goodpasture's syndrome, to skin basement membrane in individuals with pemphigoid syndrome, and to collagen in rheumatoid arthritis. The pathologic progression of the disease involves the deposition of specific antibodies to normal constituents in the skin, kidneys, lungs or joints, followed by destruction of the basement membranes by complement activation and by cellular inflammatory processes. These processes result in tissue destruction that accelerates with age, and which current treatments can ameliorate but not control or cure.

Many of the molecules that stimulate the accumulation of immune cells at a site of inflammation are products of the activated complement system. For example, component C3 is proteolytically activated to C3b, which attaches to the membrane target to be destroyed. The portion of C3 that is removed, a 9 kd peptide from the alpha chain of C3 designated C3a, is a key attractor of monocytes and macrophages to sites of tissue destruction.

Accordingly, therefore, there is a need in the art for agents which can inhibit the formation of such active components to control the processes which ultimately lead to the destruction of tissues in autoimmune diseases. The present invention fulfills this need and further provides other related advantages.

SUMMARY OF THE INVENTION

Briefly stated, the present invention provides a variety of methods for screening for (detecting or monitoring) cancers or treating cancers, or autoimmune disorders, in which complement C3 protein or a C3 related protein is associated, or, in another aspect, cancers in which certain complement regulator or complement receptor proteins or related proteins are associated. The diagnostic methods may be used on a one-time basis when an abnormality is suspected, or on a periodic basis, e.g., to monitor an individual with an elevated risk of acquiring or reacquiring cancer.

In one aspect, the present invention provides a method of screening for a cancer which comprises the step of detecting in a sample the presence of complement C3 protein or a C3 related protein, or a nucleic acid molecule encoding the protein (i.e., complement C3 or a C3 related protein). In preferred embodiments, the cancer that is screened for is a colorectal cancer, a renal cancer, a bladder cancer or a cervical cancer.

In a related aspect, the present invention provides a method of treating a cancer which comprises the step of modulating complement C3 protein or a C3 related protein associated with the cancer. In preferred embodiments, the cancer that is treated is colorectal cancer, renal cancer, bladder cancer or cervical cancer.

In another aspect, the present invention provides a method of treating an autoimmune disorder which comprises the step of modulating complement C3 protein or a C3 related protein associated with the autoimmune disorder.

In another aspect, the present invention provides a method of screening for a cancer which comprises the step of detecting in a sample the presence of one or more of complement decay acceleration factor (DAF) protein or a DAF related protein, a complement Factor I (CFI) protein or a CFI related protein, complement binding protein CR1 or a CR1 related protein, complement binding protein CR3 or a CR3 related protein, or a nucleic acid molecule encoding any one of the above proteins. In preferred embodiments, the cancer that is screened for is a colorectal cancer, a renal cancer, a bladder cancer or a cervical cancer. In preferred embodiments, the molecule detected is CFI protein or a CFI related protein, or a nucleic acid molecule encoding the protein; or CR3 protein or a CR3 related protein, or a nucleic acid encoding the protein.

In a related aspect, the present invention provides a method of treating a cancer which comprises the step of modulating any one of complement decay acceleration factor (DAF) protein or a DAF related protein, complement Factor I (CFI) protein or a CFI related protein, complement binding protein CR1 or a CR1 related protein, or complement binding protein CR3 or a CR3 related protein, wherein the protein is associated with the cancer. In preferred embodiments, the cancer that is treated is a colorectal cancer, a renal cancer, a bladder cancer or a cervical cancer. In preferred embodiments, CFI protein or a CFI related protein is modulated; or CR3 protein or a CR3 related protein is modulated.

In a related aspect, the present invention provides an agent that modulates complement C3 protein or a C3 related protein associated with cancer, for use as a medicament to treat a cancer in which complement C3 protein or a C3 related protein is associated. A composition of the present invention comprises such an agent in combination with a pharmaceutically acceptable carrier or diluent. Within the present invention, such an agent is used for the manufacture of a medicament for the treatment of a cancer in which complement C3 protein or a C3 related protein is associated.

In a related aspect, the present invention provides an agent that modulates complement C3 protein or a C3 related protein associated with an autoimmune disorder, for use as a medicament to treat an autoimmune disorder in which complement C3 protein or a C3 related protein is associated. A composition of the present invention comprises such an agent in combination with a pharmaceutically acceptable carrier or diluent. Within the present invention, such an agent is used for the manufacture of a medicament for the treatment of an autoimmune disorder in which complement C3 protein or a C3 related protein is associated.

In a related aspect, the present invention provides an agent that modulates any one of complement decay acceleration factor (DAF) protein or a DAF related protein, complement Factor I (CFI) protein or a CFI related protein, complement binding protein CR1 or a CR1 related protein, or complement binding protein CR3 or a CR3 related protein, for use as a medicament to treat a cancer in which the protein is associated. A composition of the present invention comprises such an agent in combination with a pharmaceutically acceptable carrier or diluent. Within the present invention, such an agent is used for the manufacture of a medicament for the treatment of a cancer in which the protein is associated. In preferred embodiments, the agent modulates CFI protein or a CFI related protein; or modulates CR3 protein or a CR3 related protein.

These and other aspects of the present invention will become evident upon reference to the following detailed description and attached drawings.

DETAILED DESCRIPTION OF THE INVENTION

Figure 1:
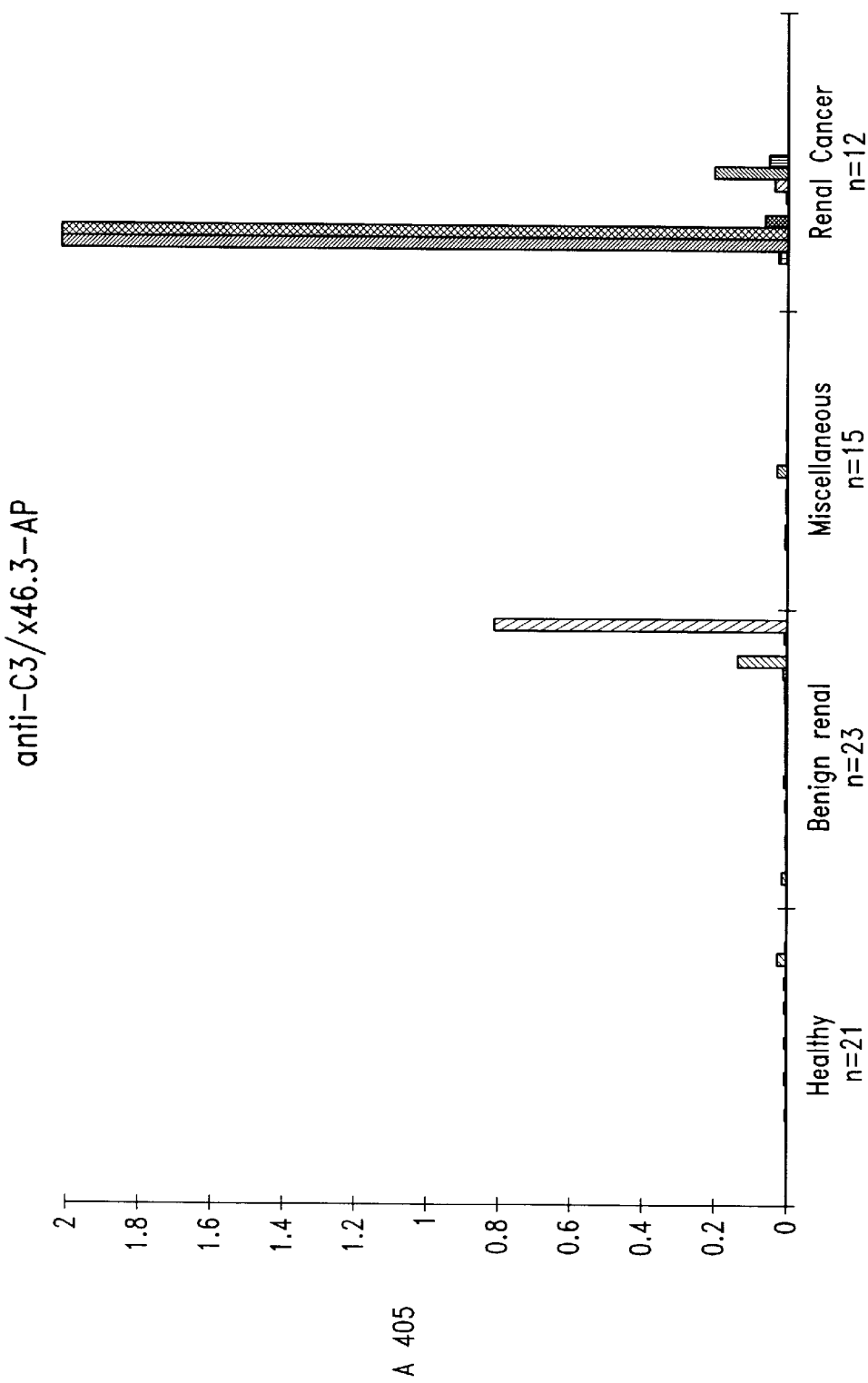
FIG. 1 illustrates an enzyme immunoassay for the detection of renal cancer that employs anti-C3 and alkaline phosphatase-conjugated MAb X46.3. The presence of MAb X46.3 was detected by measuring the absorbance at 405 nm (A405) following the addition of substrate for alkaline phosphatase.

The tumor-associated protein antigens and nucleic acid sequences screened for or modulated in the present invention have been determined, by apparent molecular weights, by sequence comparisons, by amplicon size and by restriction mapping to be related to human complement proteins C3, Factor I, Decay Accelerator Factor, or Complement Receptors CR1 or CR3. Since cancer cells may produce more than one form of any of these protein, the terms "complement related protein" and "complement receptor related protein," as used herein, refer to variants of the human complement and complement receptor proteins. The variants may be the result of mutations, alternate splicing or recombination events that alter nucleic acid molecules encoding the human complement and complement receptor proteins. In general, the amino acid sequence identity between a human complement related protein or complement receptor related protein from a tumor cell and the corresponding human complement protein or human complement receptor protein will be at least about 50%. More typically, the amino acid sequence identity will be at least about any integer from (and including) 50% to 100%, such as at least about 55%, 60%, 65%, 70%, 75%, 80%, 85%, 90% or 95% identity. Variants that are nearly identical to a human complement protein or a human complement receptor protein have at least about 85% or 90% identity. As used herein, amino acid sequence "identity" is determined by the alignment of amino acid sequences and establishment of identical amino acid residues using the program Gene-Jockey II (1993) for Macintosh (Philip L. Taylor, published by Biosoft, Cambridge, UK). The program is run in the amino acid homology mode, using program default parameters. In the comparison of two sequences aligned by the program, the percent identity is calculated only for those positions where there is an amino acid residue present in both of the two sequences. In addition, a nucleic acid molecule encoding a human complement related protein or complement receptor related protein will typically hybridize under moderately stringent conditions to one or more of primer pairs, as described below. This reflects conservation of certain sequences (disclosed herein) for tumor-associated human complement related, or human complement receptor related, antigens. A protein may generally be identified as a tumor-associated human complement related, or human complement receptor related, antigen based on the ability of a nucleic acid molecule encoding the protein to hybridize under moderately stringent conditions to one or the other or more of the primer pairs, as described below. Moderately stringent hybridization conditions are well known to one in the art, and may be defined, for example, as those performed at the calculated melting temperature of the primer with the target. Based on the disclosure herein, in combination with the methodologies known in the art, it will be evident to one in the art whether a protein is a tumor-associated human complement related or complement receptor related antigen, or whether a nucleic acid molecule encodes such as protein. Listed below are the reference numbers for nucleic acid sequences coding for complement proteins.

Reference Numbers for Nucleic Acid Sequences Coding for Human Complement Proteins

| Protein | Other Designations | Locus | GenBank Accession Number |
| --- | --- | --- | --- |
| C3 | Not Applicable | HUMC3 | K02765 |
| CR1 | CD35 | HSCR1 | M74280 |
| CR2 | CD21 | HUMCR2 | M64280 |
| CR3 | CD11b, MAC1 | HUMLAPA | M18044 |
| DAF | CD55 | HUMDAF | M15799 |
| CFI | Not Applicable | HUMFISP | J02770 |

As noted above, the present invention in one aspect is directed toward methods of screening for (detecting or monitoring) or treating an abnormality (such as cancers or autoimmune disorders) in which complement C3 or a C3 related protein is associated. As disclosed in the present invention, complement C3 or C3 related protein(s), "C3rp," has been found to be associated with the presence of tumor cells and found to survive in detectable concentrations in specimens from patients with tumors. The present disclosure describes, for example, the presence of elevated C3/C3rp (i.e., tumor C3 or C3rp) in the urine of bladder cancer patients and the synthesis of C3/C3rp by tumor cells in culture. Monoclonal antibodies which recognize C3/C3rp were prepared by immunization with partially purified protein fractionated from the urine of bladder cancer patients by heparin agarose chromatography. Monoclonal antibodies raised against normal blood C3 do not distinguish C3rp from C3.

C3/C3rp may be isolated in substantially pure form. Briefly, for example, urine samples are clarified (e.g., by centrifugation) and concentrated (e.g., by hollow fiber concentrator). The concentrated sample is chromotagraphed on heparin agarose, and bound material (bound directly or indirectly to heparin agarose) eluted using a linear buffered NaCl gradient. Pooled fractions are concentrated. C3/C3rp may be further purified using an antibody against C3/C3rp. Purity can be assessed by sodium dodecyl sulfate-polyacrylamide gel electrophoresis ("SDS-PAGE") with appropriate protein stains. Approximate molecular weights of polypeptides are estimated by comparison of their mobility to the mobility of polypeptides of known molecular weights on SDS-PAGE. C3/C3rp has substantial sequence homology to normal human blood complement C3.

Purified antigen (C3/C3rp), partially purified antigen or biological samples containing antigen may be used to produce antibodies that specifically bind to the antigen. Antibodies that specifically bind are those with an affinity of about $10^6$ liters/mol or greater. Either polyclonal antibodies or monoclonal antibodies may be generated. Polyclonal antibodies may be produced by immunization of an animal and subsequent collection of its sera. It is generally preferred to follow the initial immunization with one or more booster immunizations prior to sera collection. Monoclonal antibodies are generally produced by the method of Kohler and Milstein (*Nature* 256:495–497, 1975; *Eur. J. Immunol.* 6:511–519, 1976). Briefly, the lymph nodes and/or spleens of an animal injected with antigen in pure or impure form are fused with myeloma cells to form hybrid cell lines ("hybridomas" or "clones"). Each hybridoma secretes a single type of immunoglobulin specific for the antigen and, like the myeloma cells, has the potential for indefinite cell division.

Antigen in pure or impure form ("immunogen") is used for the immunization. Preferably, the animals are immunized with at least 100 ng each of the immunogen, most preferably greater than 500 ng each. For immunization, the immunogen may be adsorbed to a solid phase matrix, preferably to nitrocellulose paper. The paper is then introduced into the animal. Techniques for introduction of the adsorbed antigen preparation include implantation (U.S. Pat. No. 4,689,220) or solubilization of the solid phase and injection of the solubilized material (Knudsen, *Anal. Biochem.* 147:285–288, 1985). The solid phase matrix may be solubilized in an appropriate organic solvent (e.g., DMSO) and either mixed with adjuvant or saline, or injected directly.

Alternatively, the immunogen may be injected in the absence of a solid matrix and/or adjuvant. Injection or implantation may be intraperitoneal, intra-foot pad, subcutaneous, intramuscular or intravenous, but preferably intraperitoneal. The animals may also be injected with antigen complexed with adjuvant, such as Freund's adjuvant. Single or multiple booster immunizations are used. Between one and seven days prior to the fusion date, preferably on days one through four, intravenous injections of the immunogen may be given daily.

Between one and seven days, preferably four days, after the administration of the final booster immunization, spleens or portions thereof are harvested from the immunized animals. At this time, the lymph nodes may also be harvested and included in the cell preparation. The harvested organs are minced using techniques which disrupt the structure of the organ, but which are not detrimental to the lymphocytes. The organs are preferably minced with scissors, passed through a mesh screen and mixed with growth medium to enrich the preparation for lymphocytes. The minced and strained tissue is harvested by centrifugation, then mixed with growth medium to form a cell suspension. The red blood cells may be lysed by adding a hypotonic or hypertonic solution to the cell suspension. A preferred method for cell lysis is to add distilled water to the suspensions and quickly return the suspensions to an isotonic state with a hypertonic sodium chloride solution. Any remaining tissue may be removed by filtration through gauze.

The harvested cell suspension is then mixed with a myeloma cell line, preferably one which is syngeneic with the immunized animal. Myeloma cell lines from various species are widely available through, for example, American Type Culture Collection (ATCC), Rockville, Md. Myeloma cell lines commonly used include P3X63Ag8 (ATCC TIB 9), SP2/0-Ag14 (ATCC CRL 1581), FO (ATCC CRL 1646) and 210-RCY-Ag1 (Galfre et al., *Nature* 277:131, 1979).

The myeloma cells are cultured in an appropriate mammalian cell growth medium, a variety of which are generally known in the art and available from commercial sources. Mammalian cell lines are routinely grown between 36° C. and 40° C. under conditions which maintain an optimal pH between 6.0 and 8.0, preferably about pH 7.2. pH may be maintained through the use of a variety of buffer systems known in the art. A preferred buffer system involves growing the cells in a bicarbonate buffer in a humidified incubator containing $CO_2$, preferably about 7% $CO_2$.

The fusion between the lymphocytes from the immunized animal and the myeloma cells may be carried out by a variety of methods described in the literature. These methods include the use of polyethylene glycol (PEG) (Brown et al., *J. Biol. Chem.* 255:4980–4983, 1980) and electrofusion (Zimmerman and Vienken, *J. Membrane Biol.* 67:165–182, 1982). An electrofusion generator is commercially available from Biotechnologies and Experimental Research, Inc., San Diego, Calif.

Following the fusion, the cells are plated into multi-well culture plates, preferably 96-well plates. A reagent which selectively allows for the growth of the fused myeloma cells over the unfused cells is added to the culture medium. A preferred selection technique uses HAT (hypoxanthine, aminopterin, thymidine) selection. Other selection techniques may also be used depending on the myeloma cell line chosen.

Alternative methods of producing monoclonal antibodies utilize in vitro immunization techniques. Lymphocytes may be harvested from lymphoid organs, such as spleen or lymph nodes, or from whole blood as peripheral blood lymphocytes. The lymphocytes are put into culture in the presence of the appropriate immunogen. Often immunostimulatory polypeptides will be added to the culture medium concurrently. At various times following the culturing of the lymphocytes in vitro, the lymphocytes are harvested and fused with a myeloma cell line as described above.

Other techniques for producing and maintaining antibody secreting lymphocyte cell lines in culture include viral transfection of the lymphocyte to produce a transformed cell line which will continue to grow in culture. Epstein-Barr virus (EBV) has been used for this technique. EBV transformed cells do not require fusion with a myeloma cell to allow continued growth in culture.

Thymocytes may be used as a feeder layer to condition the medium for the fused cells. Alternatively, peritoneal macrophages or non-immune spleen cells may be used as a feeder layer. Another alternative is to use conditioned medium from thymocytes or macrophages. Thymocytes may be prepared from juvenile mice less than 8 weeks old. The thymus glands are harvested and minced using techniques which disrupt the thymus gland but are not detrimental to the thymocytes. This procedure is preferably carried out using scissors to mince the tissue, followed by passage of the tissue through a mesh screen. The minced and strained cell material is then harvested by centrifugation. Cell suspensions are made using growth medium. Any remaining connective tissue may be removed by filtration through gauze.

At an appropriate time following the day the cells are fused, the fused cells (hybridomas) are then analyzed for the production of antibody against the antigen. This "screening" can be done by a wide variety of techniques, including Western blot, ELISA, immunoprecipitation, effect on biological activity assays and immunocytochemical staining. These techniques and others are well described in the literature. (See, for example, J. G. R. Hurrell (ed.), *Monoclonal Hybridoma Antibodies: Techniques and Applications*, CRC Press Inc., Boca Raton, Fla., 1982.) Introduction of a screening procedure permits further definition of antibodies of useful reactivity. For example, antigen purified from a biological sample of a patient with a bladder cancer may be used in any of the above-named techniques to define antibodies which react, for example, to determinants which are common to patients with the disease.

Hybridomas which secrete antibodies of interest are maintained in culture. The cells are expanded in culture and at the same time may be cloned in such a manner as to obtain colonies originating from single cells. This provides for the monoclonal nature of the antibodies obtained from the hybridomas. A wide variety of techniques exist for cloning cells, including limiting dilution, soft agar cloning and fluorescence-activated cell sorting.

Once clones of cells are obtained, they are re-assayed for the production of the antibody of interest. These cells are then expanded in culture to allow for the production of larger amounts of the antibody. Methods for expansion of the cells include maintaining the cells in culture, placement of the cells in a bioreactor or other type of large-scale cell culture environment, or culturing the cells using various agar or gelatin carrier matrices. Antibodies are then isolated from the cell culture media.

Antibodies may be purified from conditioned media or ascites fluid by a variety of methods known in the art. These methods include ammonium sulfate precipitation, ion exchange chromatography (see Hurrell, ibid.) and high pressure liquid chromatography using a hydroxylapatite support (Stanker et al., *J. Immunol. Methods* 76:157, 1985). A preferred method for purifying antibodies from conditioned media or ascites fluid utilizes a commercially available Protein A-Sepharose® CL-4B column or Protein G Sepharose® (Pharmacia, Piscataway, N.J.; Sigma, St. Louis, Mo.) or ABX mixed ion exchange resin (JT Baker, Phillipsburg, N.J.). Antibodies may be purified with these columns using conditions suggested by the manufacturer.

As disclosed herein, C3/C3rp is found to be associated with a variety of cancers, including colorectal, renal, bladder and cervical cancers, and may be detected in a variety of ways, including by detecting C3/C3rp itself or a nucleic acid molecule encoding C3/C3rp. Methods for detecting the presence (i.e., qualitative or quantitative) of C3/C3rp include those based on physical properties, immunological properties, biochemical properties and combinations thereof (e.g., physical size of the molecule, nucleic acid sequence, amino acid sequence, binding by monoclonal or polyclonal antibodies, ligand binding, enzymatic properties, and combinations thereof). For example, regarding biochemical properties, C3/C3rp can be degraded (e.g., proteolytically activated) to produce C3b. The production of C3b may be measured directly (e.g., using an anti-C3b antibody) or indirectly (e.g., by the ability of C3b to promote the lysis of target cells).

Alternatively, rather than detecting C3/C3rp itself, a nucleic acid molecule encoding C3/C3rp can be detected. Such a nucleic acid molecule may be a deoxyribonucleic acid (DNA) or a ribonucleic acid (RNA). Generally, a nucleic acid molecule encoding for C3/C3rp is detected by amplification of the nucleic acid. A variety of methods may be utilized in order to amplify a selected sequence, including, for example, RNA amplification (see Lizardi et al., *Bio/Technology* 6:1197–1202, 1988; Kramer et al., *Nature* 339:401–402, 1989; Lomeli et al., *Clinical Chem.* 35(9):1826–1831, 1989; U.S. Pat. No. 4,786,600), and DNA amplification utilizing ligase chain reaction ("LCR") or polymerase chain reaction ("PCR") (see U.S. Pat. Nos. 4,683,195, 4,683,202, and 4,800,159) (see also U.S. Pat. Nos. 4,876,187 and 5,011,769, which describe an alternative detection/amplification system comprising the use of scissile linkages), or other nucleic acid amplification procedures that are well within the level of ordinary skill in the art. With respect to PCR, for example, the method may be modified as known in the art. Transcriptional enhancement of PCR may be accomplished by incorporation of bacteriophage T7 RNA polymerase promoter sequences in one of the primary oligonucleotides, and immunoenzymatic detection of the products from the enhanced emitter may be effected using anti-RNA:DNA antibodies (Blais, Appl. *Environ. Microbiol* 60:348–352, 1994). PCR may also be used in combination with reverse dot-blot hybridization (Iida et al., *FEMS Microbiol. Lett.* 114:167–172, 1993). PCR products may be quantitatively analyzed by incorporation of dUTP (Duplaa et al., *Anal. Biochem.* 212:229–236, 1993), and samples may be filter sampled for PCR-gene probe detection (Bej et al., *Appl. Environ. Microbiol.* 57:3529–3534, 1991).

Primers for the amplification of a selected sequence should be selected from sequences that are highly specific to C3/C3rp and form stable duplexes with the target sequence. The primers should also be non-complementary, especially at the 3' end, should not form dimers with themselves or other primers, and should not form secondary structures or duplexes with other regions of DNA. In general, primers (such as those described in greater detail below) of about 20 to 30 nucleotides are preferred, and can be easily synthesized using techniques well known in the art. PCR products, and other nucleic acid amplification products, may be quantitated using techniques known in the art (Duplaa et al., *Anal. Biochem.* 212:229–236, 1993; Higuchi et al., *Bio/Technology* 11:1026–1030).

A preferred embodiment involves assaying for the presence of specific messenger RNA (MRNA) encoding C3/C3rp. More specifically, for example, as described herein, a cell sample may be lysed and the mRNA isolated, amplified and examined for the presence of MRNA specific for C3/C3rp. A variety of procedures may be used to detect the presence of antigen-specific MRNA. A particularly preferred method includes RT-PCR (Reverse Transcriptase based Polymerase Chain Reaction) amplification of MRNA.

Detecting the presence of C3/C3rp in a sample (for example, a cell or tissue, a fecal specimen, a voided urine sample, or material extracted from a cervical swab) has a variety of uses. For example, the present invention may be used for diagnostic purposes to screen warm-blooded animals, such as humans, for cancers such as colorectal cancer, renal cancer, bladder cancer or cervical cancer (depending upon the source of the particular sample). Preferred sample sources for a particular cancer would be evident to one of ordinary skill in the art. For example, using a voided urine sample, one may screen for renal or bladder cancer. In a similar manner, the present invention may be used to monitor warm-blooded animals. In particular, a preferred use is to follow patients who have been previously diagnosed and treated for colorectal cancer, renal cancer, bladder cancer or cervical cancer. Patients who are in remission (or may in fact be cured) can be monitored for the reappearance of colorectal, renal, bladder or cervical cancer. It may be desirable to use the present invention in conjunction with one or more other tests for colorectal, renal, bladder or cervical cancer to confirm positive or negative results obtained from use of the present invention.

As disclosed herein, it appears that the production of C3/C3rp by cancers serves a beneficial purpose for the cancers. Although not intending to be bound by theory, C3/C3rp may be serving as a "decoy" that interferes with the operation of the complement system (thus permitting tumor cells to escape surveillance by the host's immune system); or the C3/C3rp production and degradation may result in product(s) that serve as a growth factor (i.e., an autocrine function) for tumor cells. Irrespective of the exact function (s) of C3/C3rp in tumor cells, the present invention provides for the modulation of C3/C3rp as a means of treating cancers. As used herein, the term "treating" cancer refers to one or more of a variety of beneficial effects, including, for example killing tumor cells, arresting the growth of a tumor, or prolonging the survival time of a tumor host. It will be evident to those of ordinary skill in the art that C3/C3rp may be modulated in a variety of ways. For example, C3/C3rp may be modulated by interrupting the production of C3/C3rp by tumor cells or "inactivating" C3/C3rp (e.g., blocking C3/C3rp, its conversion or its effect) following production by tumor cells. A preferred method of interrupting the production of the antigen is by use of DNA, or PNA (peptide nucleic acid), constructs with base sequence complementary to the antigen's MRNA. Such an approach is generically termed antisense technology. Typically, the C3/C3rp antisense DNA is inserted into an appropriate vector (virus) which delivers it to the tumor cells. Once inside the target cells, the antisense construct specifically binds to MRNA coding for the C3/C3rp, thereby preventing its translation. Primary among other methods which may be used to interrupt production of the antigen is the use of specific molecules which block the transcription of the specific gene or genes coding for the C3/C3rp. Chemicals designed to block the ability of the tumor cell to produce antigen are preferably delivered in the vicinity of the tumor, rather than systemically.

Another approach to antigen modulation is to use reagents to inhibit the activity of, or interfere with the binding sites on, C3/C3rp. One family of such reagents includes monoclonal antibodies, or fragments thereof (e.g., antigen binding fragments). As disclosed herein, for example, an appropriate concentration of an antibody which is reactive with C3/C3rp increases the rate of lysis of cancer cells by one of the complement pathways (Example III). With such reagents, as with those described above, delivery is preferably administered to the tumor site, rather than systemically. For the antibodies described above, reagent affinities should be at least about $10^6$ liters/mole and doses should be within the range of about 0.01 $\mu$g/kg body weight to 10 mg/kg body weight. In addition, the preferred type of tumor to be treated in this manner would be distinctly separate from the circulatory system. An antibody may be replaced, or supplemented, with a small organic molecule or amino acid based molecule (such as a peptide) with similar functional properties to the antibody. Thus, C3/C3rp may be modulated such that the killing of cancer cells by the complement system is promoted.

The present invention also provides for the modulation of C3/C3rp as a means for treating autoimmune disorders. It is well known that the lysis of normal cells by the immune system is a significant source of tissue destruction associated with autoimmune disorders and myocardial infarcts. Typically, for example, autoimmune antibodies deposit on a basement membrane or cell surface in the vicinity of a joint or bursa, resulting in the local activation of the classical complement pathway. C3 is a central element for both complement pathways (i.e., classical and alternative) after its proteolytic activation to form C3b. As disclosed herein, an appropriate concentration of an antibody which is reactive with C3/C3rp inhibits the conversion of C3 to C3b, thereby preventing lysis of targeted cells. Alternative binding partners (in addition to antibodies) include small organic molecules and amino acid based molecules such as peptides. Thus, molecules which bind to C3/C3rp may be used to inhibit C3-mediated cell destruction.

In another aspect of the present invention, as disclosed herein, proteins related to: decay accelerator factor (DAF) or DAF related proteins ("DAFrp"), complement Factor I (CFI) or CFI related proteins ("CFIrp"), complement binding protein CR1 or CR1 related proteins ("CR1rp") and complement binding protein CR3 or CR3 related proteins ("CR3rp") are found to be associated with a variety of cancers, including bladder, renal and cervical cancers. However, other components of the alternative complement pathway, such as factors B, D, F, P and Bb, are not found to be associated with tumor cells. DAF, DAFrp, CFI, CFIrp, CR1, CR1rp, CR3 or CR3rp may be detected in a variety of ways. For example, one or more of DAF, DAFrp, CFI, CFIrp, CR1, CR1rp, CR3 and CR3rp may be detected, or a molecule encoding one or more of these proteins may be detected. Methods for detecting the presence (i.e., qualitative or quantitative) of one or more of DAF, DAFrp, CFI, CFIrp, CR1, CR1rp, CR3 or CR3rp include those based on physical properties, immunological properties, biochemical properties and combinations thereof (e.g., physical size of the molecule, nucleic acid sequence, amino acid sequence, binding by monoclonal or polyclonal antibodies, ligand binding, enzymatic properties, and combinations thereof). The above discussion, in the context of C3/C3rp, regarding assays and the production of antibodies is incorporated here by reference for the purposes of DAF, DAFrp, CFI, CFIrp, CR1, CR1rp, CR3 and CR3rp. Furthermore, anti-DAF antibodies, anti-CFI antibodies, anti-CR1 antibodies and anti-CR3 antibodies are commercially available from, respectively, Biodesign International (Kennebunk, ME), The Binding Site (San Diego, Calif.), Pharmingen (San Jose, Calif.) and Pharmingen (San Jose, Calif.). In addition, a portion of CR3/CR3rp, such as the CD11b polypeptide chain subunit of CR3, may be detected.

Detecting the presence of DAF, DAFrp, CFI, CFIrp, CR1, CR1rp, CR3 or CR3rp in a sample has a variety of uses. For example, the present invention may be used for diagnostic purposes to screen warm-blooded animals, such as humans, for cancers such as bladder cancer, renal cancer or cervical cancer (depending upon the source of the particular sample). Similarly, the present invention may be used to monitor warm-blooded animals. In particular, a preferred use is to follow patients who have been previously diagnosed and treated for bladder cancer, renal cancer or cervical cancer. Patients who are in remission (or may in fact be cured) can be monitored for the reappearance of colorectal, renal, bladder or cervical cancer. It may be desirable to use the present invention in conjunction with one or more other tests for colorectal, renal, bladder or cervical cancer to confirm positive or negative results obtained from use of the present invention.

As disclosed herein, it appears that the production of DAF, DAFrp, CFI, CFIrp, CR1, CR1rp, CR3 or CR3rp serves a beneficial purpose for the cancers. One or more of these molecules may be interfering with the complement system, thus permitting tumor cells to escape surveillance by the host's immune system. The present invention provides for the modulation of one or more of DAF, DAFrp, CFI, CFIrp, CR1, CR1rp, CR3 or CR3rp as a means of treating cancers. It will be evident to those of ordinary skill in the art that these proteins may be modulated in a variety of ways. For example, one or more of these proteins may be modulated by interrupting the production by tumor cells or "inactivating" following production by tumor cells. For example, by use of an antibody that binds to one of these proteins and blocks the protein's activity, the rate of lysis of cancer cells by one of the complement pathways may be increased. An antibody may be replaced, or supplemented, with a small organic molecule or amino acid based molecule (such as a peptide) with similar functional properties to the antibody. At the level of the gene, expression of one or more of these proteins may be inhibited by use of antisense DNA or PNA (peptide nucleic acids). Thus, DAF, DAFrp, CFI, CFIrp, CR1, CR1rp, CR3 or CR3rp may be modulated such that the killing of cancer cells by the complement system is promoted. The above discussion, in the context of C3/C3rp, regarding cancer treatment and antigen modulation, is incorporated here by reference for the purposes of DAF, DAFrp, CFI, CFIrp, CR1, CR1rp, CR3 or CR3rp.

The following examples are offered by way of illustration and not by way of limitation.

EXAMPLES

Example I

Development of Monoclonal Antibodies

A. Antigen

The antigen source for immunization was a pool of Heparin-Agarose fractionated urines from clinically diagnosed bladder cancer patients. Twenty-four hour urine samples were centrifuged in a Beckman centrifuge (Fullerton, Calif.), Model #J2-21, S/N 5539, using a JA-10 rotor at 6,000 rpm for 20 minutes. The clarified urine sample was then concentrated using an Amicon stirred cell, 76 mm, (cat#5124) fitted with a YM30 membrane MWCO 30,000 dalton (Amicon, cat#13742) or a Microgon hollow fiber concentrator, 50,000 MWCO (cat#M15S-260-01N) to approximately 100× concentration. The concentrated sample was diluted 1:2 with 25 mM Tris-HCl pH 7.4 and loaded onto a column of Heparin-Affigel (BioRad, Richmond, Calif., cat#153-6173), equilibrated in 25 mM Tris-HCl pH 7.4, at a flow rate of 2.0 ml/min. The sample was followed with equilibration buffer until the $A_{280}$ elution profile returned to background. Bound material was eluted with a linear NaCl gradient from 0 to 250 mM NaCl in 25 mM Tris-HCl pH 7.4. Eight ml fractions were collected and fractions from the trailing half of the elution peak were pooled. Pooled fractions were concentrated with an Amicon stirred cell, 43 mm (cat#5122), fitted with a YM30 membrane, MWCO 30,000 dalton (cat#13722). Fractions comprising the pooled antigen are shown below:

| Pool I | |
|---|---|
| Patient 1 | fractions 13–31 |
| Patient 1 | fractions 14–30 |
| Patient 2 | fractions 11–19 |
| Patient 3 | fractions 11–24 |
| Pool II (1.5 mg/ml) | |
| Pool I | 1 ml |
| Patient 2 | fractions 11–19 1 ml |
| Patient 3 | fractions 11–24 1 ml |
| Patient 4 | fractions 11–20 1 ml |

B. Immunizations

Five female BALB/c mice, of 8–10 weeks of age, were immunized intraperitoneally with 0.2 ml of a 1:1 emulsion of Pool II in Freund's Complete Adjuvant (Difco, Detroit, Mich.). Three weeks later, booster immunizations of 0.1 ml containing 10 µg of protein of an emulsion in incomplete Freund's Adjuvant was administered to the rear footpads and peritoneum. Ten days later each mouse was sampled for antibody response via retro-orbital bleeds and the sera were tested via an ELISA described below for titers. Mouse number 340 showed the highest titer and was chosen for fusion four days after boosting in the footpads and peritoneum with 15 µg of Pool II in phosphate buffered saline.

C. Fusion

Four days after the last immunization animal #340 was sacrificed, the popliteal and inguinal lymph nodes and the spleen were collected and used for fusion. Fusion was carried out by a modification of the method of Fazekas De St. Groth and Scheidigger, *J. Immunol. M* 35:1–21, 1980. The parent hybridoma line FO (ibid.), obtained from the ATCC, was used for fusion, at a ratio of one to five lymphocytes. PEG-DMSO (Sigrna, St. Louis, Mo.) fusogen was used, and the cells plated out in Iscove's Modified Dulbecco's Medium (IMDM) with penicillin-streptomycin and hypoxanthine/thymidine (HT) supplement at a density of $2 \times 10^4$ cells/well with $2.58 \times 10^3$ peritoneal macrophages from unimmunized BALB/C mice added as feeders. The fusion was divided into two parts, in the first part forty-eight 96 well plates were seeded at the above density in media containing 1% fetal bovine serum (FBS). The second part consisted of 49 plates seeded at the same density in media containing 10% FBS. A total of 97 plates, or 9,312 wells were used. The plates were incubated at 37° C. in 7% $CO_2$ at 100% humidity. The next day 100 µl of selective media consisting of IMDM-HT with 2× methotrexate ($8 \times 10^{-7}$ M) and appropriate FBS concentration was added. The plates were returned to the incubator and not disturbed for six days. On day seven the plates were removed from the incubator and approximately 150 µl of media was removed via aspiration with a sterile eight place manifold. Complete IMDM with HT and appropriate FBS was added to each well using a Brinkman eight place pipette. The plates were returned to the incubator for another five to six days before screening. The fusion plates were examined each morning for wells showing growth levels suitable for screening, and were analyzed that day.

Within one week of the fusion, the plates containing the 1% FBS medium were clearly lagging in growth, and were therefore supplemented to 10% FBS. Thereafter, those wells selected from the plates initially plated in 1% FBS were designated as MOFI-followed by a number indicating the order of selection, those from the 10% FBS plates were designated with the MOFX prefix.

D. Post-Fusion Cell Culture

Wells selected via the screening assays were immediately transferred to 24 well plates containing 1 ml of complete IMDM containing 10% FBS. A sample of cells was also used to immediately re-clone the hybridomas by a serial limiting dilution procedure. This consisted of transferring a 10 µl sample of cells from the chosen well of the 96 well plate to the first well of a fresh 96 well plate previously filled with 100 µl of complete IMDM with 10% of a cloning supplement prepared from murine macrophages and thymocytes (Condimed, Boehringer-Mannheim Corp., Indianapolis, Ind.). Cells from the first well were serially diluted in the first column of wells by transferring 100 µl from the first well to the second, then from the second to the third, etc. The remaining 100 µl removed from the last well of the column is transferred back to the first well. The wells of the first column were then serially diluted across the plate by transfer of 50 µl of cell suspension using an 8 place pipette. Finally, 100 µl of cloning media was added to each well, and the plates incubated for approximately two weeks before subclones were ready for re-screening. Following growth in the 24 well plates, the clones were transferred to six well plates with 5–6 ml of culture media, the plates were incubated until near confluent growth was observed. A sample of the cells were removed for storage in a cryogenic freezer in 5% DMSO in FBS, and the remaining cells were transferred to a T-75 flask with 10 ml media for producing spent media for further testing.

E. Stabilization of Subclones

Subclones were again subjected to testing via ELISA (described below) incorporating an additional urine from a patient diagnosed as TCC+. Typically all subclones of a given original-evaluated well showed similar binding patterns and levels. Those showing loss of antibody production in all subclones were discarded, while those displaying loss in any examined subclone were subjected to another subcloning. This was repeated until all subclones showed comparable levels of expression. Nomenclature for each level of subcloning consisted of appending to the clone designation a period followed by the number of the selected subclone.

F. Assays

The titer assay was carried out by coating Pool II (described above) antigen adjusted to 4 µg/ml in 0.1 M carbonate buffer, pH 9.6, directly to polystyrene plates. Each well received 50 µl of coating solution and the plate was covered and incubated at 37° C. for 2 hours, after which time it was washed twice with phosphate buffered saline (PBS) in a Denley strip well washer. The plate was blocked by the addition of 100 µl of a 1% gelatin hydrolysate, 2% sucrose solution in 50 mM Tris-HCl, pH 7.5, at 37° C. for 1½ hours (all reagents from Sigma). Following blocking, the plate was again washed twice with PBS, then two-fold serial dilutions of mouse serum, starting at 1:100, into 10% normal horse serum in PBS, were added row-wise to the plate at 50 µl per well. The plate was incubated at 37° C. for 1 hour, washed 4 times in PBS, and 50 µl of affinity purified goat anti-mouse IgG- horseradish peroxidase (HRP) conjugate (Tago, Burlingame, Calif.) diluted 1:5000 in 10% horse serum in PBS added to each well. This was allowed to incubate for 1 hour at 37° C. The plate was washed with PBS 4 times, and 50 µl of substrate (K-Blue, ELISA Technologies, Lexington, Ky.) was added and the plate allowed to develop for 10 minutes at room temperature before stopping the reaction via the addition of 100 µl of 2M phosphoric acid solution in water (Sigma). The optical density of the wells were read at 450 and at 410 nm in a BioTek EL311 plate reader. Readings which were off scale at 450 nm were calculated from the corresponding reading at 410 nm by the method of Madersbacher and Berger, *J. Immunol M.* 138:121–124, 1991.

The fusion was screened for antibody production by use of the following fusion screen. Antibody binding was tested with: (a) two clinically diagnosed bladder cancer patient urines, stages T2III and T3III, (diluted 1:80), (b) two pools of normal human urines (diluted 1:15), (c) human type IV collagen (diluted to 4 µg/ml), all dilutions in 25 mM Tris-HCl, pH 7.5, and (d) pooled human red blood cells (Gamnma Biologicals, Houston, Tex.) diluted into PBS and coated onto poly-lysine coated plates. All plates were blocked by washing with PBS with 0.1% Tween-20, and by the dilution of the media samples 1:5 into complete IMDM containing 10% FBS. Supernatant fluid (70 µl) of the wells chosen for screening were transferred to a well of a 96 well plate. To each well, 280 µl of diluent was added, and 50 µl was distributed to the test plate wells. The remaining steps of the assay were as for the titer assay, with the exception that the conjugate used was human serum adsorbed goat anti-mouse IgG-HRP conjugate (Kirkegaard and Perry Labs (KPL), Gaithersburg, Md.) diluted 1:5000 in 10% normal goat serum in PBS for all except the RBC plates. For the latter, an alkaline phosphatase conjugate of a similar antibody was used (KPL, Gaithersburg, Md.) followed by use of PNPP (p-nitrophenyl phosphate) substrate. Controls were used for each assay, negative control was fresh IMDM with 10% FBS, positive controls were monoclonal anti-human collagen (Sigma C1926), and monoclonal anti-hIga (A1.1.2.4, Bard Diagnostic Sciences, Inc., Redmond, Wash.), both of which showed high binding to all test antigens except the red blood cells. Criteria for selection were high binding to cancer urine plates (OD>1), low binding to normal urines and other test antigens (OD<0.5). Others which showed high antibody levels in different patterns with respect to the test antigens were also selected for potential research uses.

Subclones were screened by several assays. First, the fusion assay was again used then, following expansion in culture of selected subclones, an abbreviated ELISA was employed using normal urine pool I and the two advanced stage urines used in the fusion assay. The testing was carried out at dilutions of 1:10 and 1:100 for the early subclones, and an additional dilution of 1:1000 for the later subclones. In several of the subclone assays the addition of urine from a patient with a lower grade cancer was included.

From the 9,312 wells plated in the fusion, a total of 880 wells showing growth were screened, with a total of 94 X series and 24 I series clones selected for further work. Analysis of the fusion via Poisson distribution, suggested that there was a 4.6% probability that any well showing growth contained 2 or more clones, or 5 to 6 of the total clones being multiclonal. Of the 118 clones selected, 37-X and 8-I series were eventually lost due to instability or lack of growth without feeder cells.

A total of 32 subclones were selected based on selectivity of antibody binding to cancer positive urines versus the normal urines and on retention of assay OD with dilution of culture supernatant to select for high affinity and good production level. Samples of spent culture media from the following clones were evaluated for their potential utility in a clinical assay to detect antigens disclosed herein: I7.3, I8.2, I10.2, I11.1, I12.2, I17.3, X4.1, X22.2, X28.1, X44.1, X46.3, X48.1, X49.1, X49.2, X50.3, X53.2, X55.1, X56.3, X59.1, X60.2, X61.2, X62.1, X63.2, X64.3, X67.2, X69.1, X70.2, X84.2, and X87.2.

Example II

Presence in Urine of Proteins Related to Complement Factor C3

A. An ELISA Assay for the Presence of C3 or C3-Related Proteins (C3rp)

Urine specimens from five cancer patients and two normal urine pools were tested in an enzyme immunoassay format utilizing a commercially-available anti-C3 MAb, which was reactive, as well, with the activated C3, designated C3b. These samples were also tested with several monoclonal antibodies (MAbs) produced by immunizing Balb/c mice with a partially purified protein fraction from urines of human bladder cancer patients (see Example I) and identified as MOF MAbs. The normal urine pools were each composed of equal volumes from five individuals, non-randomly selected to include males, females, Caucasians, Asians and Blacks, all over the age of 40.

The urine specimens were diluted in 1 mM carbonate buffer, pH 9.6. The normal pools were diluted 1:8 and the specimens from the cancer patients were each diluted (dilutions between 1:15 and 1:80) to yield an antigen concentration of approximately 100 U/mL in the Bard BTA TRAK# assay (Bard Diagnostic Sciences, Redmond, Wash.). Each diluted specimen was pipetted into individual wells of a High-Binding 96-well microtiter plate (LabSystems, Helsinki, Finland) and allowed to incubate overnight at 2–8° C. Samples were removed from the plate by aspiration. A blocking buffer (1% gelatin hydrolysate, 2% sucrose, 50 mM Tris buffer, pH 7.5; all reagents from Sigma, St. Louis, Mo.) was then added and allowed to incubate for 1 hour at 37° C.

Various MAbs, as noted above, were diluted in Bard® BTA TRAK™ diluent (Bard Diagnostic Sciences) to a final concentration of 1 µg/mL. They were then added to individual wells and allowed to incubate for 1 hour at 37° C.. MAb solutions were then removed by aspiration and the plates were washed four times on a plate washer (BioTek, Winooski, Vt.). Next, a reporter conjugate (alkaline phosphatase-labeled goat anti-mouse IgG, human serum-absorbed, Kirkegaard and Perry Labs, Gaithersburg, Md.) at a concentration of 0.5 µg/mL in assay buffer was added to each well. After incubation for 1 hour at 37° C., the plates were again washed. Substrate [p-nitrophenyl phosphate (pNPP), 1 mg/mL, in DEA buffer (1 M diethanolamine, 0.5 mM $MgCl_2$, pH 9.8); all reagents from Sigma] was added and the plates were incubated for 30 minutes at 37° C. Reaction with the substrate was terminated by addition of stop buffer (0.1 M EDTA, pH 9.8). Developed color was measured at 405 nm on an MRX microplate reader (Dynex, Chantilly, Va.).

As controls, specificity of the MAbs was determined by reaction with protein components of the Alternative Complement pathway (C3, Factor H, Factor D, Factor B, Properdin and Factor I) and of the Classical Pathway (C1q). All complement proteins were tested at a coating level of 5 µg/ml.

The results are summarized in Table I as the absorbance measurements at 405 nm. Commercially available MAb (Sigma, St. Louis) to C3, which is also reactive with the activated C3 molecule (designated C3b), was tested on five cancer patient urine specimens (PES, GS3, GS4, GS5, OCK), each diluted to read 100 U/mL on the Bard BTA TRAK™ assay (approximately 1:15 to 1:80). The commercial anti-C3 MAb reacted strongly with C3, but was unreactive with the two normal pools, unreactive with the five specimens from bladder cancer patients, and unreactive with the other complement factors tested. In fact, all of the MAbs were unreactive with the other complement proteins, except for C1q, which is known to bind the Fc region of mouse IgG1 antibodies. In contrast, the MOF MAbs X46.3, X87.2, X67.2, and X59.1 (from Example I) are all reactive with one or more of the five patient specimens and surprisingly the C3 antigen, but unreactive with the normal urine pools and the other complement proteins (again with the exception of C1q, to which most of the MAbs show at least some level of reactivity, presumably due to binding of the Fc region of the MAb to the C1q).

TABLE I

MOF MAbs vs Complement Proteins and TCC+ Urines
Absorbance at 405 nm

| MOF MAb | NP-1 | NP-2 | C3 | FH | PES | GS-3 | GS-4 | GS-5 | FI | FD | FB | FP | Clq | OCK |
|---|---|---|---|---|---|---|---|---|---|---|---|---|---|---|
| X4.1 | 0.003 | 0.003 | >3.5 | 0.039 | 0.193 | 0.012 | 1.160 | 0.735 | 0 | 0.009 | 0.001 | 0.002 | 0.051 | 0.075 |
| X22.2 | 0.015 | 0.018 | >3.5 | 0.033 | 0.152 | 0.028 | 1.216 | 0.993 | 0.019 | 0.029 | 0.021 | 0.019 | 0.078 | 0.284 |
| X28.1 | 0.015 | 0.014 | >3.5 | 0.014 | 0.083 | 0.044 | 0.844 | 0.647 | 0.014 | 0.032 | 0.018 | 0.005 | 0.036 | 0.163 |
| X46.3 | 0 | 0 | >3.5 | 0.050 | 0.399 | 0.014 | 2.024 | 1.282 | 0 | 0.003 | 0 | 0 | 0.086 | 0.237 |
| X59.1 | 0.039 | 0.044 | >3.5 | 0.025 | 0.070 | 0.542 | 0.431 | 0.302 | 0.041 | 0.084 | 0.041 | 0.037 | 0.151 | 0.125 |
| X60.2 | 0.005 | 0.008 | >3.5 | 0.008 | 0.038 | 0.015 | 0.342 | 0.326 | 0.011 | 0.016 | 0.010 | 0.002 | 0.032 | 0.023 |
| X61.2 | 0.010 | 0.006 | >3.5 | 0.007 | 0.060 | 0.009 | 0.811 | 0.614 | 0.013 | 0.011 | 0.004 | 0 | 0.028 | 0.130 |
| X64.3 | 0.015 | 0.016 | >3.5 | 0.015 | 0.055 | 0.031 | 0.767 | 0.559 | 0.016 | 0.032 | 0.016 | 0.004 | 0.051 | 0.136 |
| X87.2 | 0.003 | 0.004 | >3.5 | 0.016 | 0.244 | 0.019 | 1.394 | 0.892 | 0.006 | 0.010 | 0.021 | 0.007 | 0.080 | 0.356 |
| I 8.2 | 0.314 | 0.422 | 0.026 | 0.350 | 0.787 | 0.518 | 1.879 | 1.537 | 0.013 | 0.022 | 0.161 | 0.005 | 0.072 | 1.468 |
| anti-C3 (Sigma) | 0.003 | 0.003 | >3.5 | 0.009 | 0.012 | 0.076 | 0.051 | 0.024 | 0.014 | 0.007 | 0.010 | 0.009 | 0.729 | 0.024 |

B. Enzyme Immunoassay (EIA) for Detection of Renal Cancer

A sandwich EIA was constructed utilizing commercially-obtained anti-C3 (BioDesign, Kennebunk, Me.) and alkaline phosphatase-conjugated MAb X46.3. Antibodies were purified by chromatography on immobilized Protein G or Protein A by standard techniques. Although antibody-enzyme conjugates could be prepared using a variety of coupling techniques (for review see Scouten, W. H., *Methods in Enzymology* 135:30–65, 1987), a minor variation of a method described by S. Hashida and E. Ishikawa (*Anal. Lett.* 18, B9:1143–1155, 1985) was used. Briefly, purified monoclonal antibodies were treated with excess N-acetylhomocysteine thiolactone (AHTL) at neutral pH to introduce reactive thiol groups, and then desalted to remove excess AHTL. Separately, alkaline phosphatase (AP) was treated with excess sulfosuccinimidyl 4-(N-maleimidomethyl) cyclohexane- 1-carboxylate to introduce maleimido groups, and excess reagent was removed by desalting. The conjugates were prepared by mixing antibody and enzyme derivatives, which became covalently coupled via thioether bonds. Any excess maleimido groups were then capped by reaction with cysteamine.

96-Well microtiter plates were coated with anti-C3 at a concentration of 5 µg/mL in carbonate buffer and blocked, as described above in Example I.A for plates coated with urine specimens and complement proteins.

Urine samples from healthy donors, from patients with bladder or renal cancer, or from those with non-cancerous renal diseases were diluted 1:50 in carbonate buffer (25 mM pH 9.6) and added to the antibody-coated plates. After incubation at 37° C. for 1 hour, the samples were aspirated from the wells, which were then washed four times with Bard BTA TRAK™ wash buffer using a Dynatech (Chantilly, Va.) plate washer. The alkaline phosphatase-conjugated MAb X46.3, at a concentration of 1.0 µg/mL in Bard BTA TRAK™ assay diluent, was added to each well (100 µL per well). Plates were then incubated at 37° C. for 1 hour, aspirated and washed as above, and substrate was added (pNPP at 1 mg/mL in DEA buffer; Sigma). After incubation at 37° C. for 30 minutes, followed by addition of 100 µL of stop buffer, the wells were measured at 405 nm on the Dynatek MRX plate reader.

The results shown in FIG. 1 demonstrate a sensitivity of 58% for renal cell cancer (RCC) with a specificity of 95%, derived from four false positives out of a total of 77 non-renal cell cancer specimens.

C. Expression of C3-Related Proteins by Cancer Cell Lines and Human Cancer Tissues as Indicated by Antibody Binding Immunohistochemical analysis of a number of cell lines was performed to test for the presence of the C3-related antigen which is bound by MAb X46.3. Cell lines and primary cultures were obtained from ATCC (Bethesda, Md.) or Clonetics Corporation (San Diego, Calif.) except for Pastor and CAKI cells, which were provided by Dr. R. Vessella (Laboratory of Tumor Immunology, University of Washington Medical Center, Seattle, Wash.), and hybridoma cell liens, which were from Bard Diagnostic Sciences.

Cells were grown in culture with specifications for media as defined by ATCC and were harvested by trypsin-EDTA treatment (0.25% trypsin, 10 mM EDTA; reagents from Sigma) after the cells had reached a confluence of 90% or greater. Cells were counted in a hemacytometer by standard methods using a phase contrast microscope (American Optical). After aliquots were removed for counting, the cells were pelleted at 1000×G at room temperature.

Cell pellets were prepared for staining with MAbs by quick freezing in liquid nitrogen. The frozen pellets were sectioned on a cryostat microtome (Bartles & Stout) and then fixed in cold acetone (−20° C.) for 15 minutes. Fixed sections were blocked by treating with 25% horse serum before staining. The primary MAb (X46.3; ATCC Accession No. HB-12064, American Type Culture Collection, Rockville, Md.) was diluted to a concentration of 2 µg/mL in phosphate-buffered saline (PBS), pH 7.2, and incubated on the sections for 30 minutes at room temperature. After three washes with PBS, the conjugated secondary MAb (goat anti-mouse IgG peroxidase conjugate, human serum absorbed, Kirkegaard and Perry Laboratories, Gaithersburg, Md.), at a concentration of 0.25 µg/mL in PBS, was incubated on the slide at room temp for 30 minutes. Following three washes with PBS, the specimens were developed with 3,3'-diaminobenzidine (DAB). Unless otherwise indicated all reagents were from Sigma Chemical.

As shown in Table II, staining with MAb X46.3 revealed surprisingly the presence of the target antigen (C3 or C3rp) in a number of cancer cell lines.

TABLE II

Production of Human C3/C3rp by Various Cell Lines

| Cell Line | Tumor Source | IHC (MAb X46.3) |
|---|---|---|
| RCC7860 | Renal Cancer | Neg |
| ACHN | Renal Cancer | Neg |
| Pastor | Renal Cancer | 4+ |
| 769P | Renal Cancer | Neg |

TABLE II-continued

Production of Human C3/C3rp by Various Cell Lines

| Cell Line | Tumor Source | IHC (MAb X46.3) |
|---|---|---|
| CAKI-1 | Renal Clear Cell Cancer | 1+ |
| HL60 | Myeloid | Neg |
| LSI74T | Colon Adenocarcinoma | Neg |
| T24 | TCC, Bladder | Neg |
| 5637 | Primary Bladder Cancer | 3+ |
| RT4 | Papillary Bladder Cancer | 4+ |
| J82 | TCC, Bladder | 1+ |
| 486P | TCC, Bladder | 2+ |
| NHEK | Normal human epithelial keratinocytes (not an established cell line) | Neg |
| X44.1 | Mouse Hybridoma | Neg |
| X46.3 | Mouse Hybridoma | Neg |

Example III

Effect of Anti-C3RP Antibodies on Stability of C3B and Lysis of Target Cells

A. In Vitro Protection of C3b by Anti-C3rp MAbs

Reactions were performed by incubating 1 μg of Factor H with either 15 or 30 μg of MAb, in 20 μL of PBS for 30 minutes at 37° C., followed by the addition of 7.5 μg of C3b and 5 μg of Factor I into each reaction tube (final reaction volume 32.5 μL). (C3b was generated from C3 by the method of Pangbum, M. K., and Mueller-Eberhard, H. J., *Biochemistry* 22:178–185, 1983.) The mixture was then incubated on a rotator at 37° C. for 1 hour. Results were determined by SDS-PAGE of the reaction mixtures under reducing conditions (50 mM DTT) on a 4–12% gradient gel (Novex, San Diego, Cailf.). (Unless specified otherwise, all reagents are from Sigma, St. Louis, Mo.) The gel was scanned with a BioRad GelDoc scanner. The intensities of the bands measured in this way were converted to percentage of C3b remaining. Two control lanes were included. The one containing the reaction mixture in the absence of MAb was used to represent 100 percent degradation, while the other containing the reaction mixture with no Factor H was used to represent 0 percent degradation.

Figure 2:
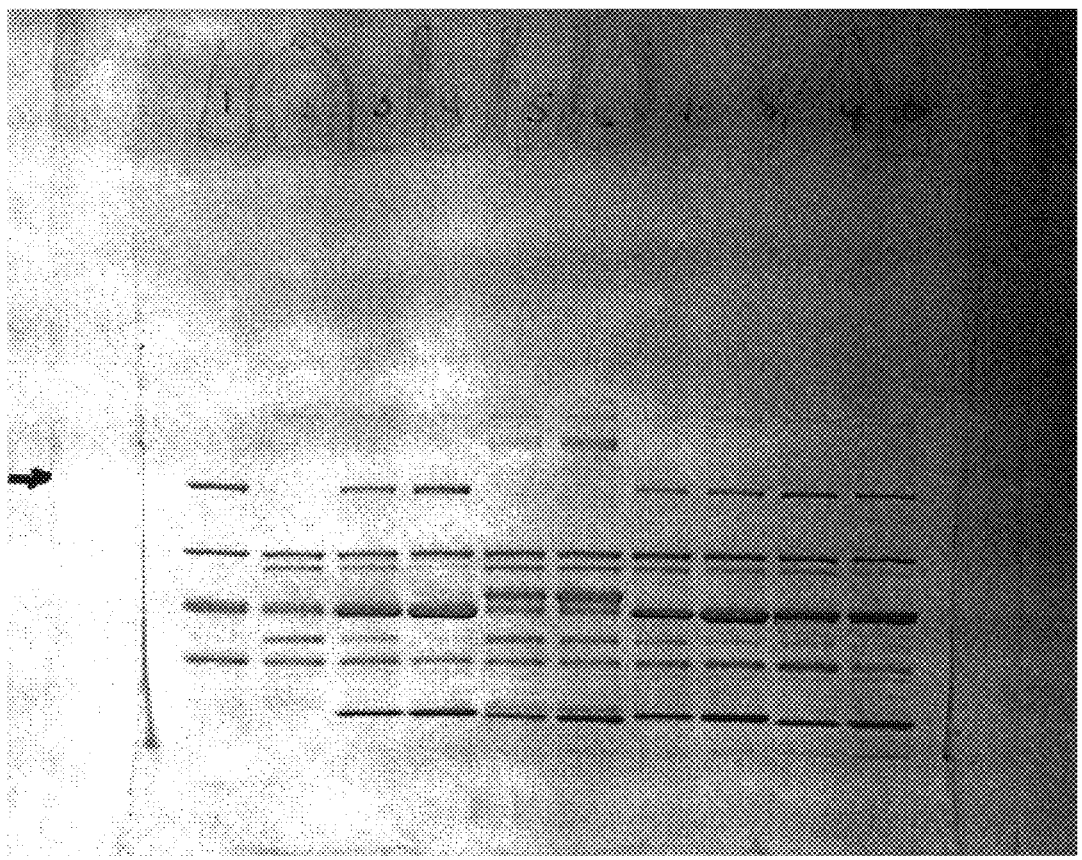
FIG. 2 shows a photograph of an SDS-PAGE gel demonstrating the inhibition of C3b degradation by MAb X46.3.

A photograph of the SDS-PAGE gel from the experiment described above is shown in FIG. 2. The results derived from scanning the gel are summarized in Table III. Lane 1 of the gel shows the molecular masses of C3b and Factor I. Note that C3b is 108 kD, and is uncleaved in the presence of Factor I alone. Lane 2 shows the result after addition of Factor H to the mixture of C3b and Factor I. Note the complete degradation of C3b and the appearance of a smaller 38 kD degradation product. Lanes 3 and 4 show the inhibition of C3b degradation by MAb X46.3. Rows 2 and 3 of the accompanying Table III summarize the effect of X46.3 inhibition, which is 83.7% when the reaction mixture contains 30 μg of MAb (Row 3, Column 3). Lanes 5–6 are negative controls containing antibody non-inhibitory to the Factor I/Factor H-mediated C3b degradation. Lanes 7–8 are positive controls containing anti-Factor H antibody inhibitory to the Factor I/Factor H-mediated C3b degradation. Lanes 9–10 illustrate that Mab X87.3 is also capable of inhibiting Factor H+Factor I-mediated degradation of C3b, although not as efficiently as MAb X46.3 Rows 4 and 5 of Table III summarize the effect of this inhibition by X87.3.

These results demonstrate that MAbs X46.3 and X87.3 are able to block the Factor H+Factor I-mediated degradation of complement component C3b in vitro.

TABLE III

Inhibition of C3b Degradation in the Presence of Anti-BTA MAbs

| Sample | Quantity of Sample | C3b Remaining (Percent) |
|---|---|---|
| Control, No MAb | Standard | 0 |
| X46.3 | 15 μg | 60.0 |
| X46.3 | 30 μg | 83.7 |
| X87.2 | 15 μg | 24.7 |
| X87.2 | 30 μg | 54.9 |
| Control, No Factor H | Standard | 100 |

Figure 3:
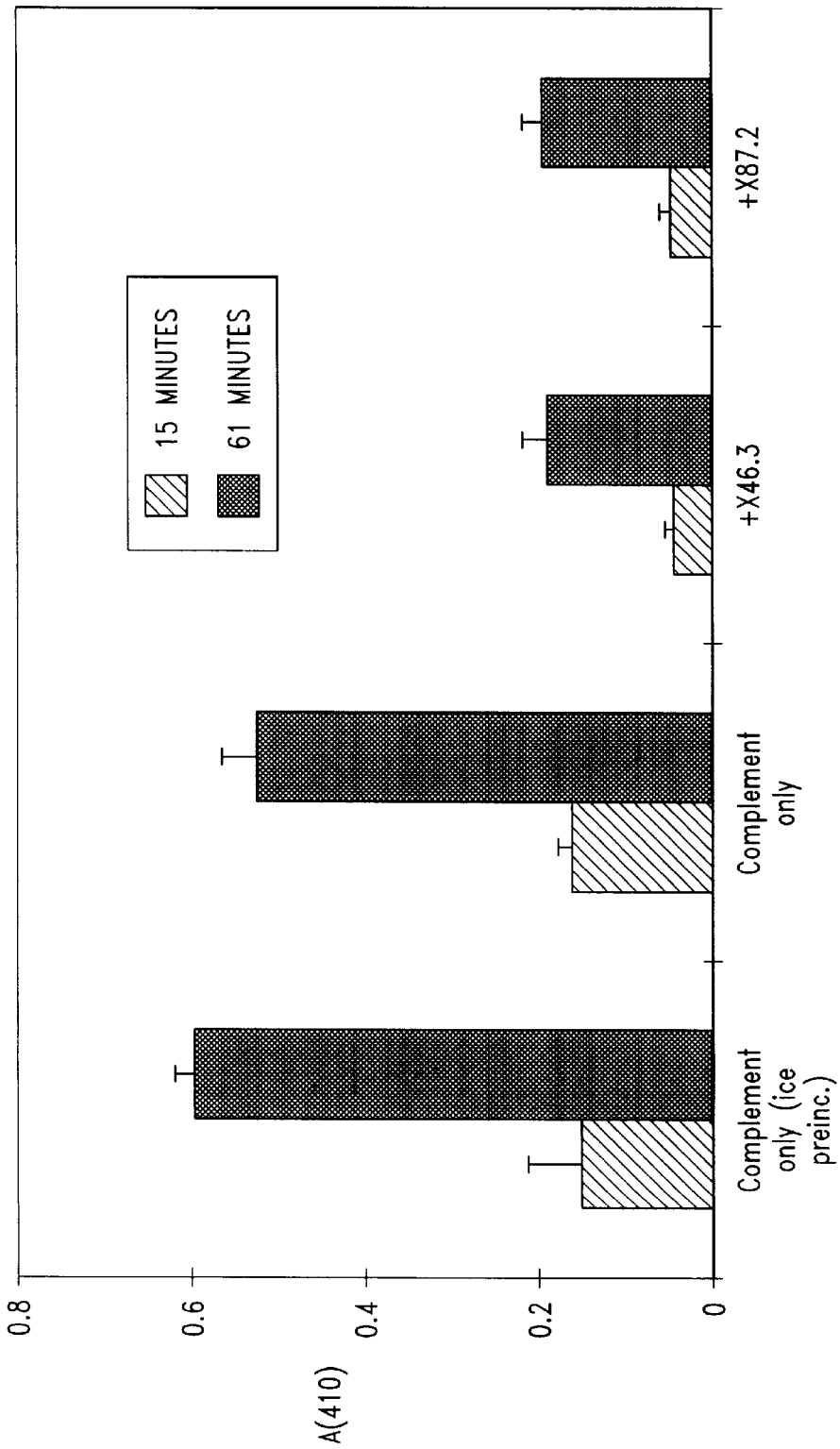
FIG. 3 illustrates the effect of MAbs X46.3 and X87.2 on complement-mediated hemolysis.

B. Protection from Cell Lysis via the Alternate Complement Pathway by MAbs Specific for Human C3-Related Protein Standard guinea pig complement was treated with EGTA to chelate calcium. Then $MgCl_2$, which is required for the activity of the alternative complement pathway (ACP), was added (all reagents form Sigma). The mixture was incubated for 20 minutes at 37° C., then added to 7E9 RBCs and further incubated at 37° C. After 45 minutes and again after 117 minutes, hemolysis was determined by reading the $A_{450}$ vs controls (on a Dynatech MR5000 96-well plate reader). Hemolysis was determined in the absence or presence of MAb X46.3 (FIG. 3). When included, the MAb was used at a concentration in the reaction mixture of 10 nM or 30 nM.

MAb X46.3, which specifically binds to C3, but does not bind to sheep, rabbit or RBCs, was shown to be effective in preventing RBC lysis in a manner dependent on the time of incubation and the concentration of the antibody. Since X46.3 does not bind to RBCs, and since RBCs do not produce C3, Factor H, Factor I or DAF, the mechanism of action of cell protection must be the binding of X46.3 to C3 in the added guinea pig complement and the resulting inhibition of the activation of C3 to C3b on the cell surface.

Example IV

Presence of Other Complement Proteins in Urine Production of Complement Regulatory Proteins by Tumors and Tumors Cell Lines A. ELISA Assays for Detection of Components of the Complement Cascade A series of ELISAs were constructed, patterned after that described in Example II.A, in order to test for the presence of proteins of the alternative complement pathway (ACP) in the urine of patients with bladder, cervical or renal cell cancer.

Purified complement proteins C1q, Factor B, Factor D, Factor F, Factor I and properdin were purchased from Quidel (San Diego, Cailf.); purified human C1q, C3, Factor B, Factor H and Factor I were purchased from Sigma (St. Louis, Mo.). C3b was produced from C3 as referenced above in Example III.A. Goat polyclonal antibodies to human C1q and C2, and monoclonal antibodies to C1q, C3b, C4bp, Bb, Factor D, Factor H, Factor I and properdin were available from Quidel (San Diego, Cailf.).

Results of the ELISAs are summarized in Table IV. Neither Factor I nor properdin were found in any urine specimen tested. The anti-C3 monoclonal antibody yielded positive results for specimens from some bladder (3/6) and renal (2/6) cancer patients, but results were negative for all cervical cancer specimens. Note that this anti-C3 MAb was not the same as the one used above in Example II.B, thus emphasizing the importance of considering the epitope specificity of MAbs to be used in diagnostic assays.

TABLE IV

Reactivity of Antibodies Specific for Complement Proteins with Specimens from Bladder, Renal and Cervical Cancers

| MAb or Antiserum | Transitional Cell Cancer | | Renal Cell Cancer | | Cervical Cancer | |
|---|---|---|---|---|---|---|
| | Number Positive | Number Tested | Number Positive | Number Tested | Number Positive | Number Tested |
| X46.3 | 6 | 6 | 6 | 6 | 5 | 6 |
| X60.2 | 2 | 6 | 1 | 6 | 0 | 6 |
| Anti-Bb | 2 | 6 | 1 | 6 | 0 | 6 |
| Anti-C3 | 3 | 6 | 2 | 6 | 0 | 6 |
| Anti-Factor I | 0 | 6 | 0 | 6 | 0 | 6 |
| Anti-properdin | 0 | 6 | 0 | 6 | 0 | 6 |

B. RT-PCR Assays for Regulatory Components of the Alternative Pathway

1. Cell and Tissue Preparations

Cells were grown in culture with specifications for media as defined by ATCC and were harvested by trypsin-EDTA treatment (0.25% trypsin, 10 mM EDTA; reagents from Sigma) after the cells had reached a confluence of 90% or greater. In some experiments, cells were harvested from parallel cultures at subconfluent densities within the ranges 10–20%, 20–50%, 50–90%, as well as >>100%. Cells were counted with a hemacytometer by standard methods using a phase contrast microscope (American Optical). After aliquots were removed for counting, cells were pelleted at 1000×G at room temperature.

Cell lines and primary cultures were obtained from ATCC (Bethesda, Md.) or Clonetics Corporation (San Diego, Cailf.), except for Pastor and CAKI cells, which were provided by Dr. R. Vessella (Laboratory of Tumor Immunology, University of Washington Medical Center, Seattle, Wash.), and hybridoma cell lines, which were from Bard Diagnostic Sciences.

2. RT-PCR cDNA was prepared from MRNA present in preparations of total cellular RNA from various cancer cell lines, using Reverse Transcriptase plus Random Hexamer primers (50 pmoles per 20 μL reaction), according to the protocol in a commercially-available RNA PCR kit (Perkin-Elmer, Foster City, Cailf.). A 2–3 μg quantity of total RNA was used for each reaction, with the polymerization temperature and time set at 42° C. and 90 minutes, respectively.

The results of the RT-PCR study are summarized in Table V. For many of these, as indicated by ±, the presence of a specific MRNA is dependent on the growth curve of the cells in culture. For example, LS174T cells at 60% to 100% confluence were consistently negative for MRNA coding for complement Factor I. Furthermore, even under the most stringent PCR conditions possible, amplicons of incorrect size were produced by the RNA isolated from many of these same cell lines.

TABLE V

Amplification of Cell Line RNA with Primers for Selected RCA Products

| Cell Line | CR1 | CR2 | CR3 | huCFH | huCFI | DAF |
|---|---|---|---|---|---|---|
| NHEK | – | – | – | – | – | – |
| HTB9 | + | – | – | + | + | + |
| HTB5 | – | – | – | + | – | – |
| HeLaS3 | ± | – | + | + | + | + |
| C4i | – | – | – | + | – | + |
| C4ii | ± | – | + | + | + | + |
| HTB33 | ± | – | + | + | + | ± |
| LS174T | ± | – | + | – | ± | + |
| PC3 | + | – | ± | + | – | + |
| HL60 | + | – | + | – | – | + |

3. Decay Accelerator Factor (DAF)

PCR of MRNA for DAF was performed with the primer pairs 797us (ATGATGAAGGAGAGTGGAGTGG)SEQ ID NO:1 and 1269ds (CTCCTTGCTCTGTTGACATTCC) SEQ ID NO:2, each used at a final concentration of 0.3 μM in the reaction mixture. Primers were synthesized by Midland Certified Reagents (Midland, Tex.) and were purified by anion-exchange chromatography. Annealing conditions were 62° C. for 30 seconds and extension was at 72° C. for 90 seconds, with 40 cycles. Positive results, defined to be the identification of a 472-base pair amplicon, were determined by electrophoresis at 90 volts for 90 minutes on 1.5% agarose gels (Sigma), followed by staining with ethidium bromide (Sigma), and destaining in deionized water.

Figure 4:
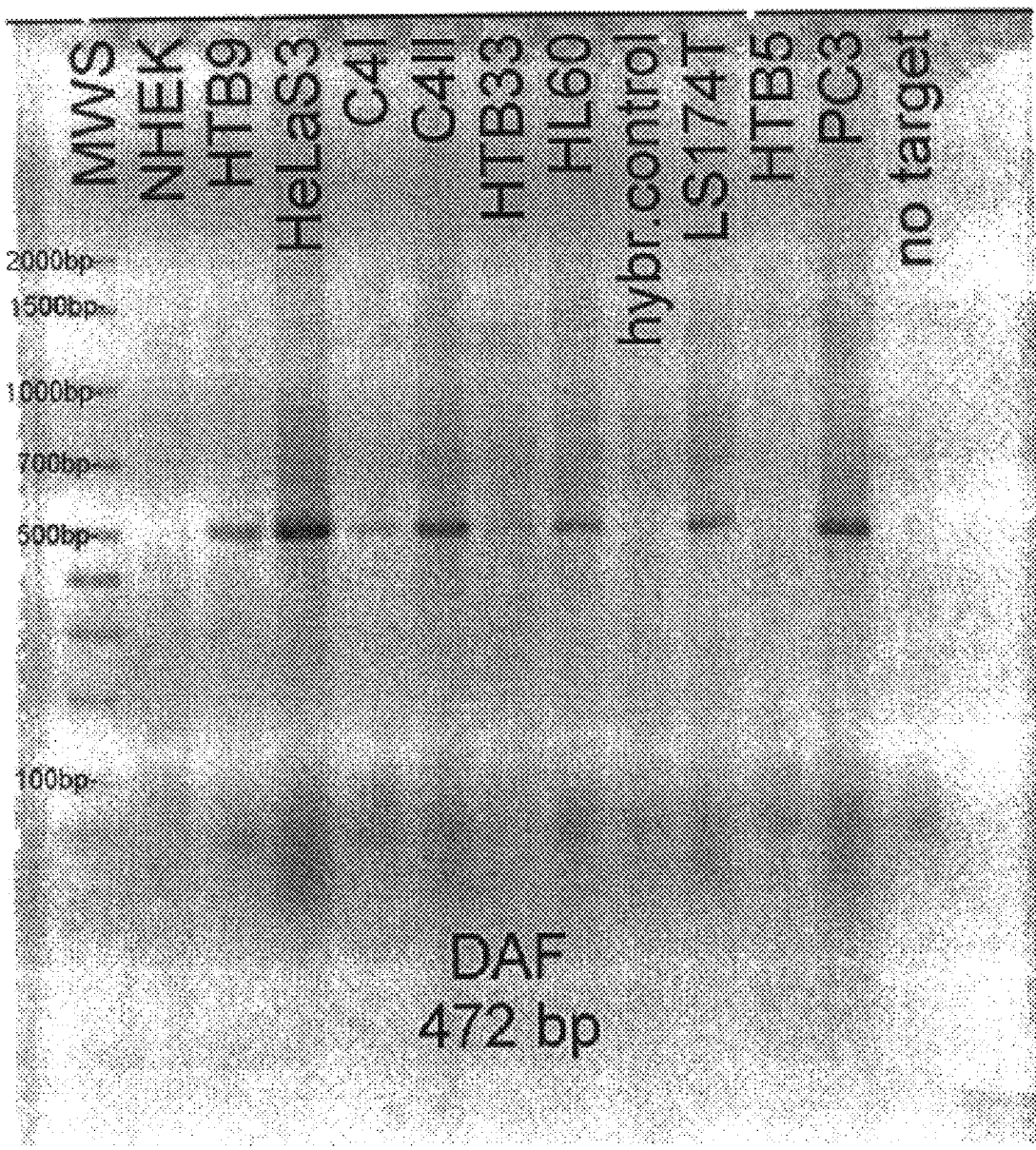
FIG. 4 shows a photograph of an agarose gel demonstrating the presence of DAF mRNA in several different human cancer cell lines.

The gel pattern reproduced in FIG. 4 shows evidence for the presence of DAF MRNA in several different human cancer cell lines.

4. Complement Receptors (CR1, CR2, CR3)

PCR of mRNA for the complement receptors was performed with primer pairs 302064 (CR1), 302065 (CR2) and 302066 (CR3), each used at 10 nmoles per 100 μL reaction mixture. Primers were purchased from Stratagene Cloning Systems (La Jolla, Cailf.). Annealing conditions were 60° C. for 60 seconds and extension was at 70° C. for 2 minutes, with 30 cycles; an additional 10 cycles were performed with the extension step set at 2 minutes and 30 seconds, followed by a final extension for 7 minutes. The size of the cDNA products were determined by electrophoresis at 90 volts for 90 minutes on 1.5% agarose gels (Sigma), followed by staining with ethidium bromide (Sigma), and destaining in deionized water. Positive results were defined to be a 521-base pair product for CR1 and ad 345-based pair product for CR3.

Figure 5:
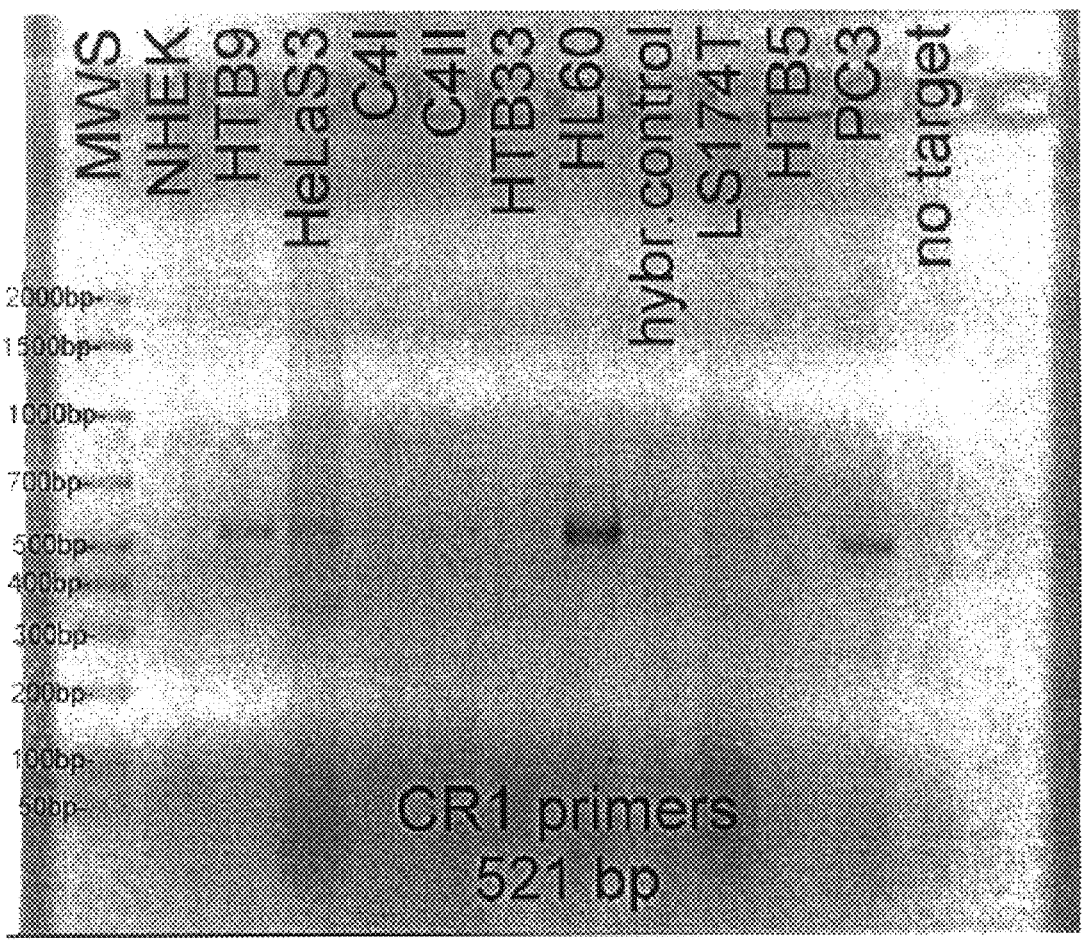
FIG. 5 shows the results for amplification of complement receptor CR1 cDNA from a variety of cell lines.
Figure 6:
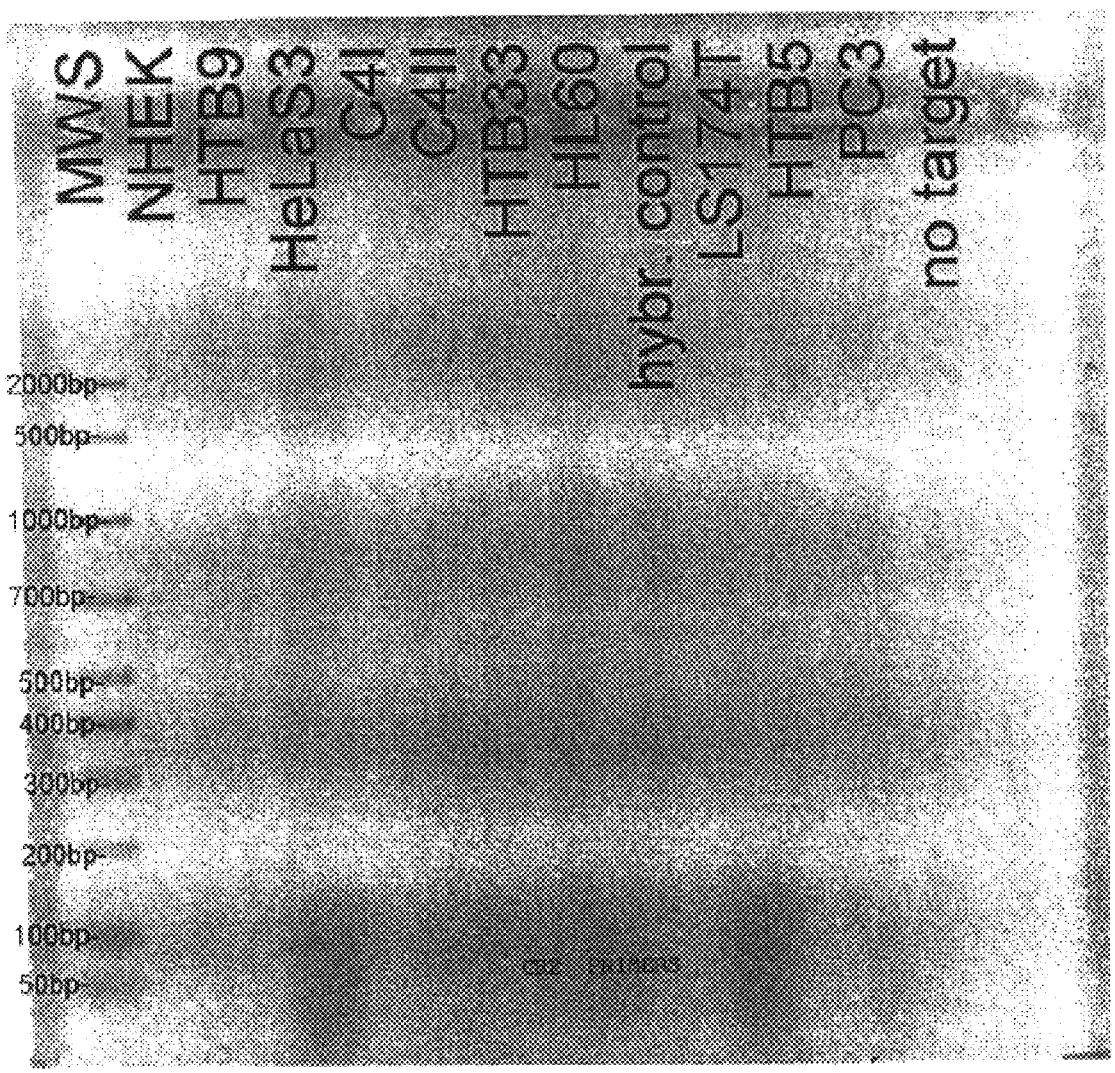
FIG. 6 shows the results for amplification of complement receptor CR2 cDNA from a variety of cell lines.
Figure 7:
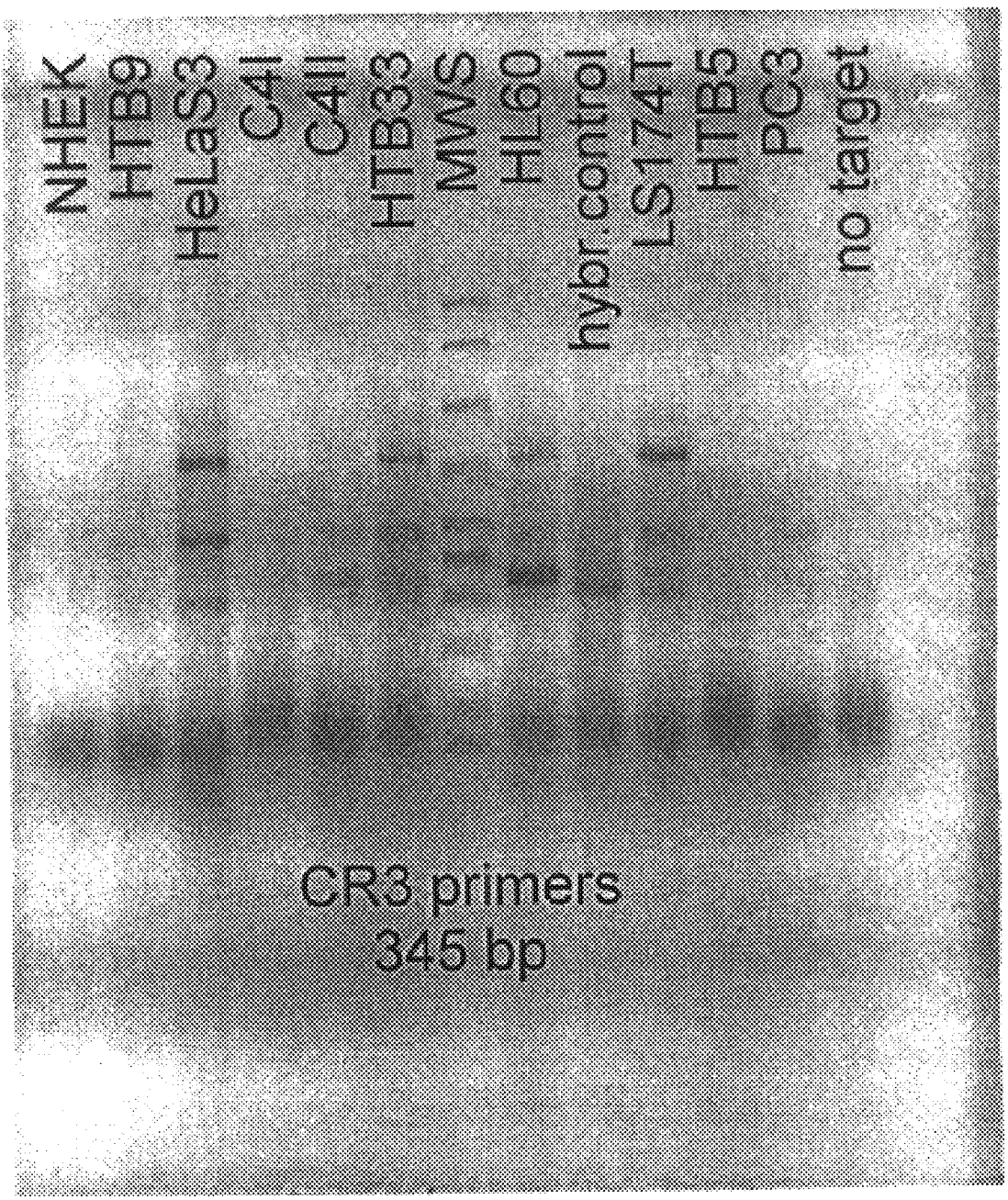
FIG. 7 shows the results for amplification of complement receptor CR3 cDNA from a variety of cell lines.

FIG. 5 (CR1), FIG. 6 (CR2) and FIG. 7 (CR3) show the results for amplification of complement receptor cDNA from a variety of cell lines. Note that all cell lines were negative for CR2. CR1 cDNA of the correct size was produced by a number of cell lines. HeLaS3 was an exception, in that a second product of unexpected size (approximately 350 base pairs) was observed. RT-PCR for CR3, a complement protein coded for in the same chromosomal locus as C3, yielded extremely heterogeneous amplicons. The HeLaS3, LS174T, HL60 and HTB33 cell lines all made products which were much larger than expected size in addition to the product of the correct size for cognate CR3.

While it is generally recognized that DAF (CD55) is widely expressed on cells of the body that are in contact with the blood, the general expression of this molecule on tumor tissues or in cancer cell lines has not been reported. Similarly, complement receptors 1 and 3 (CD35 and CD11b) have not previously been associated with expression in cancers. The role of CR1 as a negative regulator of both complement pathways and its structural relationship to DAF and factor H, two other proteins coded within the RCA gene locus, is highly significant. Upregulation of CR1 by cancer cells would augment their ability to evade lysis through either complement pathway. The role of CR3 in regulating both complement pathways by promoting the internalization of iC3b by cells bearing CD11b suggests a more general activation of complement regulators by tumor cells, since the CD11b protein is not in the RCA complex, but is instead coded for by a locus on chromosome 16.

5. Complement Factor I (CFI)

PCR of mRNA for complement Factor I was performed with the primer pair FI7us (GCAAGGTCACTTATACATCTCAAGAGC) SEQ ID NO:3 and FIG683ds (CCCATTCACACACTGAAAGAAGTCATCC) SEQ ID NO:4, each used at 0.50 nmoles per 100 μL reaction mixture. Primers were synthesized by Midland Certified Reagents (Midland, Tex.) and were purified by anion-exchange chromatography. Annealing conditions were 62° C. for 30 seconds and extension was at 72° C. for 90 seconds, with 40 cycles. Positive results, defined to be the identification of a 472-base pair amplicon, were determined by electrophoresis at 90 volts for 90 minutes on 2% agarose gels (Sigma), followed by staining with ethidium bromide (Sigma), and destaining in deionized water.

Figure 8:
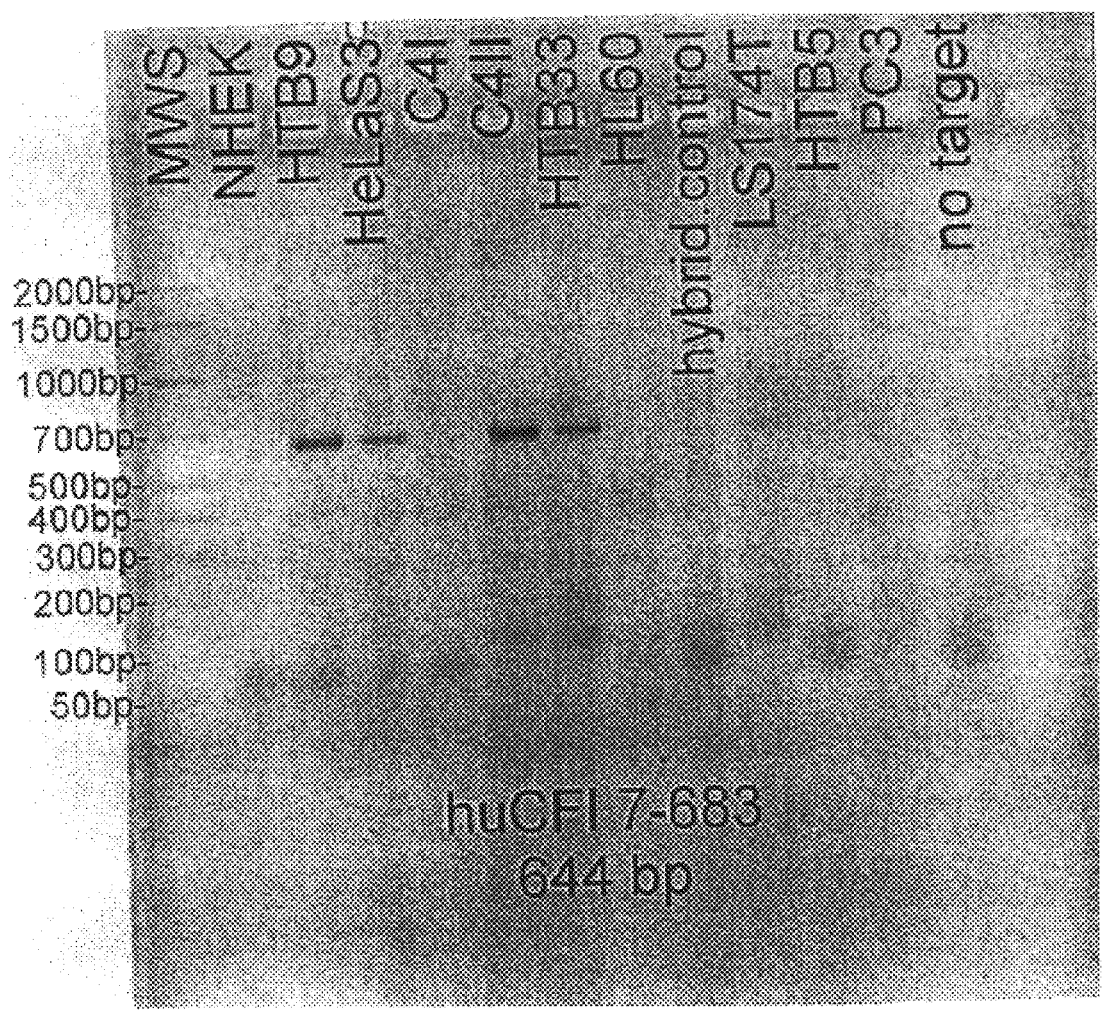
FIG. 8 shows the results for amplification of complement Factor I cDNA from a variety of cell lines.

The results of the electrophoresis are shown in FIG. 8, where the origin of the material on each lane is as follows: Lane 1, DNA molecular weight markers; Lane 2, NHEK; Lane 3, HTB-9; Lane 4, HeLaS3; Lane 5, C4i; Lane 6, C4ii; Lanes 7, HTB-33; Lane 8, HL-60; Lane 9, positive control; Lane 10, LS174T; Lanes 11, HTB-5; Lane 12, PC-3; Lane 13, no RNA target. Therefore, of the cancer cell lines represented in this experiment, one TCC line (HTB-9) and three cervical lines (HeLaS3, C4ii and HTB-33) are positive for amplicons of the correct size, while one cervical line (C4i), one colon line (LS 174T), one TCC line (HTB-5), one prostate line (PC-3) and the negative controls (NHEK and myeloblastoma HL-60) are negative.

Example V

A Cervical Cancer Marker

Reactivity of X67.2 with cervical specimens was initially identified by a dot-blot procedure. Samples were tested either neat or diluted 1:10 WITH Bard BTA TRAK™ assay diluent. All assay steps were performed at room temperature. Samples of 2 μL were applied to nitrocellulose (Millipore, Bedford, Mass.) and air dried for approximately 30 minutes, followed by blocking (as above in Example I.A) for 2 hours. The blots were rinsed once with BTA TRAK™ assay diluent. The blots were then covered with a solution of MAb X67.2, at a concentration of 1 μg/mL in assay diluent, incubated for 1 hour, and rinsed twice with assay diluent. Specimens which were reactive with the MAb were identified by incubation of the blot for 1 hour with alkaline phosphatase-conjugated goat anti-mouse IgG (Kirkegaard and Perry, human serum absorbed) at a concentration of 0.5 μg/mL in BTA TRAK™ assay diluent. Finally, development of the blot with substrate was performed as described in Example II.A.

Figure 9:
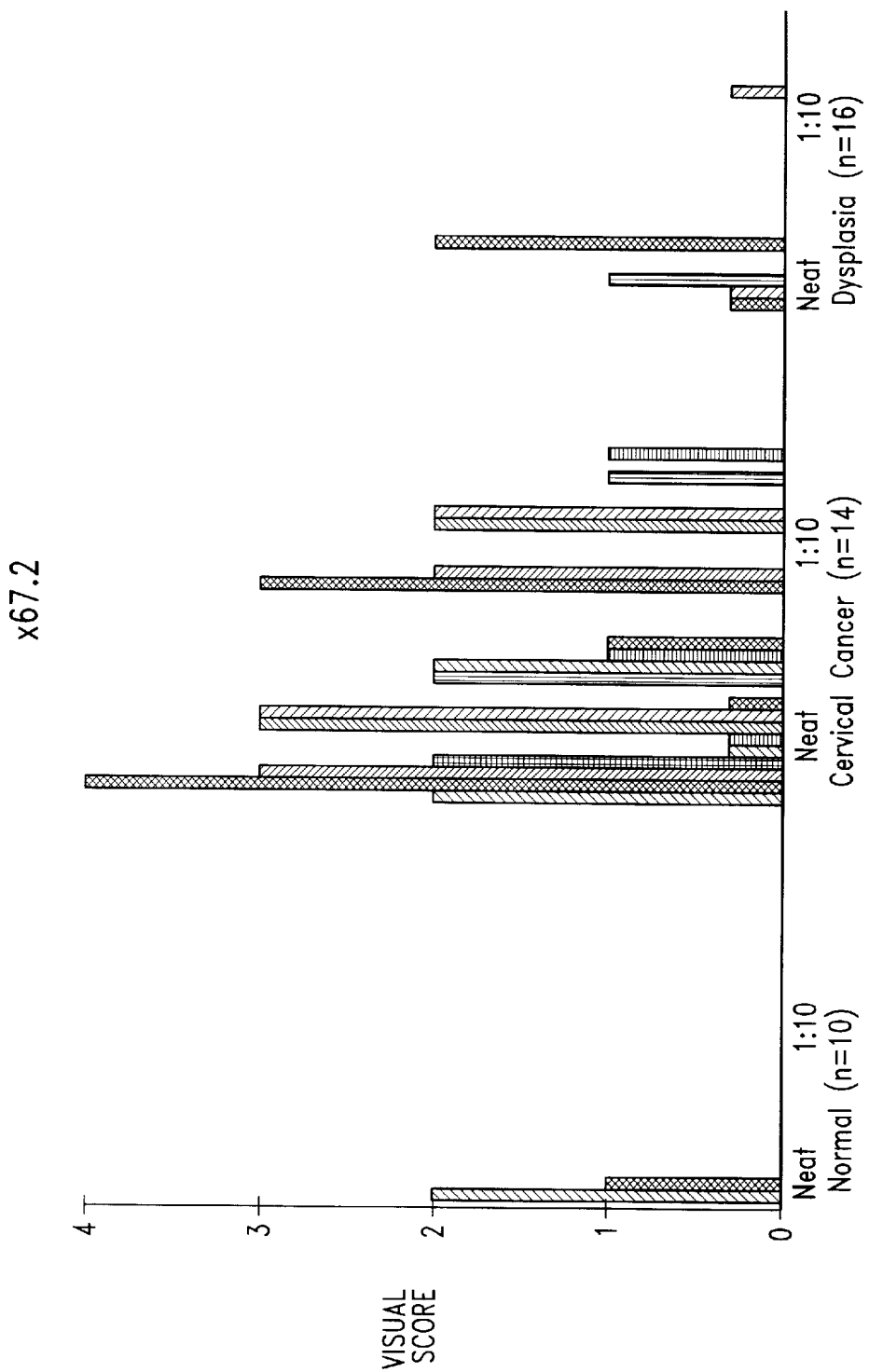
FIG. 9 illustrates the reactivity of MAb X67.2 with cervical specimens, as identified by a dot-blot procedure.

The intensity of the spots on the dot blot were scored visually, and the results are summarized FIG. 9.

When cervical swab specimens are tested by plate ELISA, as described in Example IV.A, MAb 67.2 discriminates patients with squamous cell cancer of the cervix from patients with infectious diseases, normal healthy individuals and individuals with dysplastic disease.

Example VI

Detection of Colorectal Cancer

Human complement receptor CR3 consists of two polypeptide chains, designated CD18 and CD11b. The CD18 polypeptide is also found in the complement receptor CR4. The CD11b polypeptide chain (GenBank file accession number M18044, locus HUMLAPA) is though to be a subunit only of CR3. The CD11b chain is also referred to as MAC1, reflecting the belief that the molecule is expressed specifically in circulating monocytic macrophage cells. These cells are a subset of the peripheral blood leukocyte fraction (PBL).

Figure 10:
FIG. 10 shows the results for amplification of cDNA for the CD11b chain of CR3 from a variety of human cell lines by the CD11b 18-933RT primer set.

A. A set of PCR primers (Table VI) was designed from the sequence listed in GenBank file M18044 and was used in RT-PCR reactions to amplify the MRNA isolated from the human myeloid leukemia cell line HL-60 and encoding the CD11b protein (FIG. 10). The PCR primers were synthesized by Midland Certified Reagents, Midland, Tex.

B. Conditions for amplification of CD11b MRNA from HL-60 cells.

1. Reverse Transcription of MRNA a. Total cellular RNA was prepared from cultured cells according to the method described in the manufacturer's patent insert for RNAzol (Tel-Test, Inc., Friendswood, Tex.). For cancer cell lines, suitable cell numbers were obtained by culturing cells to 90% confluency in a size T162 flask (Coming-Costar, Cambridge, Mass.), in a suitable cell culture medium, as specified by the American Type Culture Collection (ATCC, Rockville, Md.). Total cellular RNA from peripheral blood leukocytes was obtained after fractionating fresh whole blood on a gradient of Histopaque (Sigma, Catalog #1077), according to the method provided by the manufacturer, and collecting the leukocyte fraction. Ribonuclease-free deoxyribonuclease I (Boehringer-Mannheim, Indianapolis, Ind., Catalog #776785) was used, according to the manufacturer's instructions, at 1 unit per microgram of target nucleic acid, in order to remove contaminating DNA from the RNA preparations.

b. Total RNA ranging between 0.5 and 5μg, but optimally 2–3 μg, in a volume of up to 5 μL was used in each reaction. The solution of total RNA was mixed with a Reverse Transcription Master Mix (RTMM), formulated as described below. All reagents were from Perkin-Elmer Applied Biosystems, Foster City, Cailf., and may be purchased together as the Gene Amp RNA PCR Kit, Part No. N808-0017, and used as described below.

| Reverse Transcription Master Mix | | |
|---|---|---|
| Ingredient | Volume Added, μL | Working Concentration |
| 25 mM MgCl$_2$ | 4 | 5 mM |
| 10X PCR buffer | 2 | 1 X |
| dATP | 2 | 1 mM |
| dGTP | 2 | 1 mM |
| dCTP | 2 | 1 mM |
| dTTP | 2 | 1 mM |
| RNAse Inhibitor | 0.5 | 1 U/ml |
| MuLV Reverse Transcriptase (RT) | 1 | 2.5 U/ml |
| Random Hexamers | 1 | 2.5 μM | b. The 16.5 μL volume of RTMM was mixed with the solution of total RNA and the final volume adjusted to 20 μL (up to 22 μL allowable) with molecular biology grade (ribonuclease-free) water (Catalog #2-538561, 5'-3' Inc., Boulder, Colo.).

c. The reaction was performed by allowing the RTMM containing the random hexamer primers to anneal with target RNA in the sample for 15 minutes at room temperature (22° C.). The reaction mixture was then raised to 42° C. and polymerization allowed to proceed for 90 minutes.

Following this incubation, the reverse transcriptase (RT) was inactivated by heating at 99° C. for 5 minutes. The RT reaction can be performed on a suitable thermal cycler, such as the Perkin-Elmer GeneAmp Model 2400, or in a series of water baths or incubators.

2. PCR Amplification of CR3 (CD11b) cDNA a. Amplification of the cDNA resulting from the RT reaction is performed by using between 2.5 and 10 mL of the RT product. Typically, a volume of 2.5 µL of the RT product is combined with 47.5 mL of a PCR Master Mix (PCRMM), as listing below.

PCR Master Mix

| Ingredient | Volume Added, µL | Working Concentration |
|---|---|---|
| 25 mM MgCl$_2$ | 4.5 | 2.5 mM |
| 10X PCR buffer | 4.75 | 1 X |
| Upstream primer | 0.5 | 0.5–1 µM |
| Downstream primer | 0.5 | 0.5–1 µM |
| Molecular Biology Grade water | 29.5–37 | Not applicable |
| Taq Polymerase | 0.25 | 1.25 U | b. PCR amplification proceeds after the samples are mixed. First, a one minute incubation at 95° C. is used to melt any cDNA/mRNA pairs or cDNA/annealed primer pairs. Then 30 cycles are performed, each including a 94° C. melt for 20 seconds, annealing for one minute at a temperature which is unique for each primer set, as specified below, and a two-minute extension at 70° C. As necessary, up to 10 additional cycles of amplification may be performed under the same protocol as just described, except for an increase of 30 seconds in the extension time.

c. Assessment of the amplified sample is carried out by agarose gel electrophoresis. A solution of 0.5% (W/V) agarose (Sigma, Catalog #A9539) in TAE buffer (Tris-Acetate-EDTA, Sigma, Catalog #T4038) is poured into a suitable submarine gel electrophoresis chamber, such as the BioRad Sub Cell (Richmond, Cailf.). The sample to be examined can then be mixed with a suitable sample buffer such as Gel Loading Solution (Sigma, Catalog #G2526).

The sample is then electrophoresed at 90V, using a power supply such as the BioRad PowerPac 3000, until the two tracking dyes are separated. This takes approximately 90 minutes at room temperature. The electrophoresed product is then visualized by submersion of the gel into a solution prepared by adding a small amount (0.1 mL) of a saturated solution of ethidium bromide (Sigma, Catalog #E7637) in Molecular Biology Grade water to 30 mL of the TAE buffer. After staining for 15 minutes at room temperature, the gel is transferred to a clean vessel and destained with two changes TAE buffer, with a 10-minute incubation in each.

The stained amplicon can be viewed under a suitable UV source such as an Ultra-Lum Transilluminator (Carson, Cailf.).

TABLE VI

Primer Sets for Amplification of CR3 mRNA

| PRIMER | SEQUENCE |
|---|---|
| CD11b-18 (SEQ ID NO:5) | TCAGTGGTGC CTGCAACCCCT |
| CD11b-129 (SEQ ID NO:6) | TTGGACACTG AAAACGCAATG |
| CD11b-933RT (SEQ ID NO:7) | CCCAATGACG TAGCGAATGAC |

TABLE VI-continued

Primer Sets for Amplification of CR3 mRNA

| PRIMER | SEQUENCE |
|---|---|
| CD11b-922 (SEQ ID NO:8) | TACGTCATTG GGGTGGGAGAT |
| CD11b-1792RT (SEQ ID NO:9) | CTGCTATCCG CTGGCTATGG |
| CD11b-1657 (SEQ ID NO:10) | GGGGACGTAA ATGGGGACAA |
| CD11b-2588RT (SEQ ID NO:11) | CGCTGGTTCT GGAGTGTCGAC |
| CD11b-2010 (SEQ ID NO:12) | CAAGGAAGCC GGAGAGGTCAG |
| CD11b-3103RT (SEQ ID NO:13) | AGTCGGACTG AGAGGGCAAGC |
| CD11b-2665 (SEQ ID NO:14) | GCAGCATAAA CCACCCCATCT |
| CD11b-3559RT (SEQ ID NO:15) | AGGCAGCTCT GTCGGGAAGG |

Downstream primers are always designated "RT"

C. Results of RT-PCR of CR3 From Human Cancer Cell Lines and Human Peripheral Blood Leukocytes PCR amplification of total cellular RNA isolated from HL-60, a human myeloid leukemia cell line, yielded product of expected size for all of the primer sets described in Table VI.

Total cellular RNA from peripheral blood leukocytes also yielded product of the expected size. This product is presumed to be derived from the monocytic fraction of the blood cells, as the monocytes are known to comprise approximately 40% of the white cells and to make complement receptors and proteins.

In sharp contrast, as seen above in Example IV for DAF and CR3, many cancer cell lines produce mutated forms of the CR3 MRNA. The ability to amplify any product by PCR is a function of the primer set chosen. Use of the Stratagene primer sets described in Example IV resulted in no product of expected size for most cell lines. However, use of the 18M-933RT primer set described in Table VI at an annealing temperature of 65° C., not only yielded product of expected size, but also revealed the presence of a previously undescribed CD11b MRNA variant, as shown FIG. 10.

Amplification of cDNA with the 18-933 primer set is expected to yield a 915 base pair product, as shown in the gel for most cell lines tested. In addition, a product of approximately 830 base pairs is produced by a false priming of the 933RT oligonucleotide at position 853, and a 505 base pair product can be produced by a false prime at position 523. Furthermore, sequence similarities to the 18M primer can allow a false prime to occur at base positions 168, 192 and 672. All of the false priming sites have at least 4 mismatches from the correct target sequence. However, point mutations in the DNA could lead to an increased probability of a false prime, resulting in a product of an unexpected size. One way to maximize the fidelity of the priming event (the annealing step in a PCR amplification cycle) is by employing higher annealing temperatures, thus increasing the stringency of base matching requirements. A 65° C. annealing temperature was used with the 18-933 primer set in these amplifications, in contrast to annealing temperatures of 50–60° C. more typically used in PCR. Thus, point mutations that have occurred in the 18-933 priming regions would be predicted to have brought the false primed sequences into closer agreement with the cognate sequences. An alternative explanation for the presence of a product of an unexpected size is a splicing variation in the messenger RNA. Alternate splices, as they are known in the art, occur when one or more exons are deleted from an expressed gene. The resulting MRNA is smaller than the original gene product, in some cases very much smaller. A relevant example of alternate splicing occurs with the complement Factor H mRNA. Alternate splicing within factor H proteins has been reviewed by Zipfel and Skerka (*Immunology Today* 15:121–126, 1994).

Figure 11:
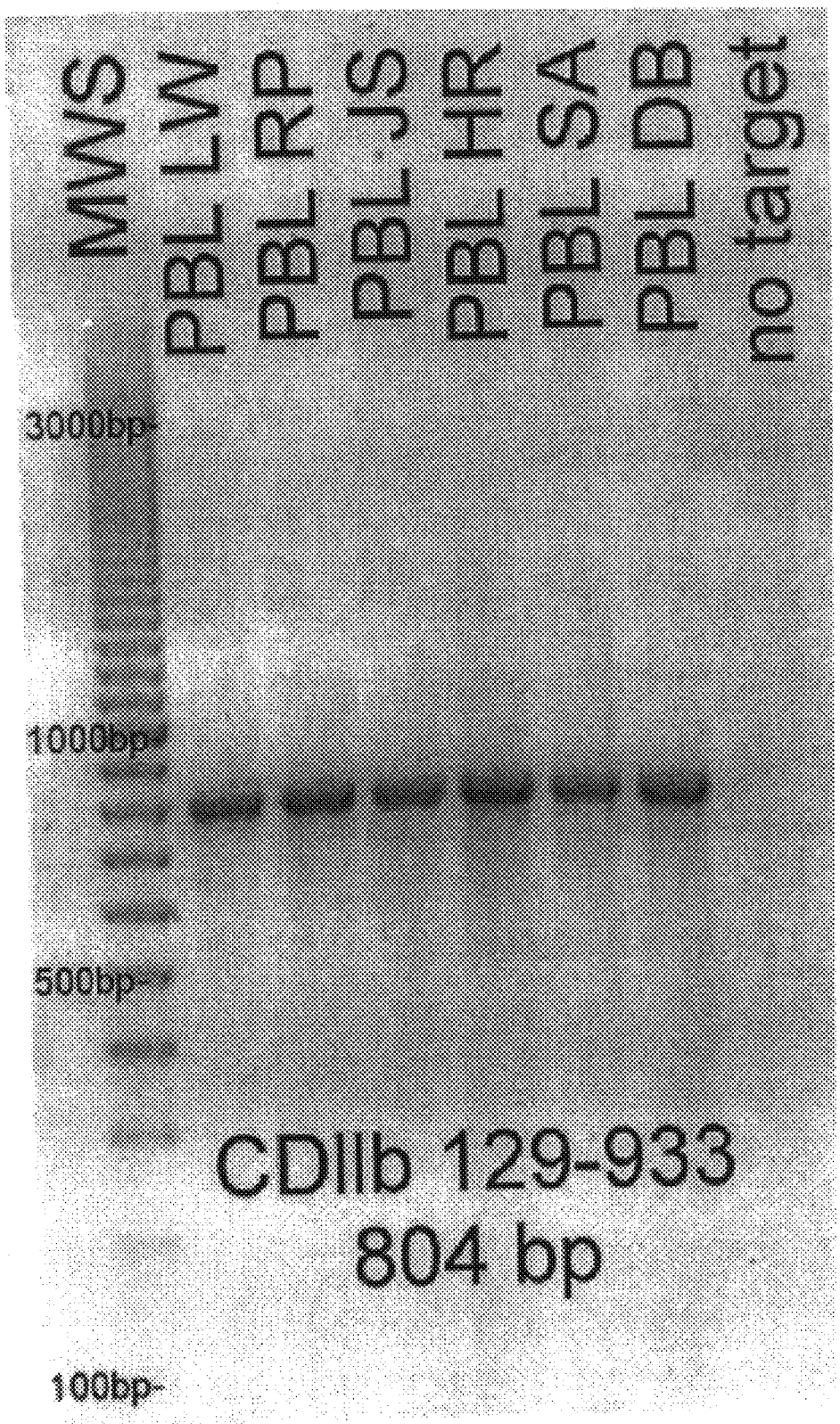
FIG. 11 shows the results for amplification of cDNA from various peripheral blood leukocyte specimens using the CD11b 18-933RT primer set.

The presence of an unexpected amplicon from the 18-933 primer set is illustrated for various cell lines in FIG. 10, in which the material in each lane is as follows, beginning from the left: Lanes 1 and 8, molecular weight markers; Lane 2, HL60; Lane 3, HTB9; Lane 4, HeLaS3; Lane 5, LS174T; Lane 6, 33CO; Lane 7, SW480; Lane 9, MCF7; Lane 10, PC3; Lane 11, C4ii; Lane 12, HTB5, Lane 13, negative control; Lane 14, no target. The unexpected amplicon is approximately 420 bases and is heavily expressed in the colon lines LS174T, 33CO, SW480; in the cervical lines HeLaS3, C4i and C4ii; and in the bladder line HTB5. The size of the amplicon can be determined by reading the 100 base pair interval molecular weight standard ladder (MWS) in FIG. 10. Note that only a small amount of this product is seen in the HL60 myeloid line. Note also that the 420 base product is the only amplicon produced by the breast cancer line MCF7 under the conditions used. FIG. 11 shows the results of amplification of cDNA from peripheral blood leukocyte specimens using the same 18-933RT primer set. The samples on the gel are as follows, beginning from the left: Lane 1, molecular weight markers; Lane 2, PBL LW; Lane 3, PBL RP; Lane 4, PBL JS; Lane 5, PBL HR; Lane 6, PBL SA; Lane 7, PBL DB; Lane 8, no target. These data illustrate that the 420 base amplicon is a minor product in the amplification PBL MRNA with this primer pair. Note, finally, the complete absence of the 850 base product during amplification of PBL MRNA. Thus, the CR3/CD11b sequence is not only expressed in cancer cell lines, an unexpected finding, but the sequence appears to be highly mutated.

Figure 12:
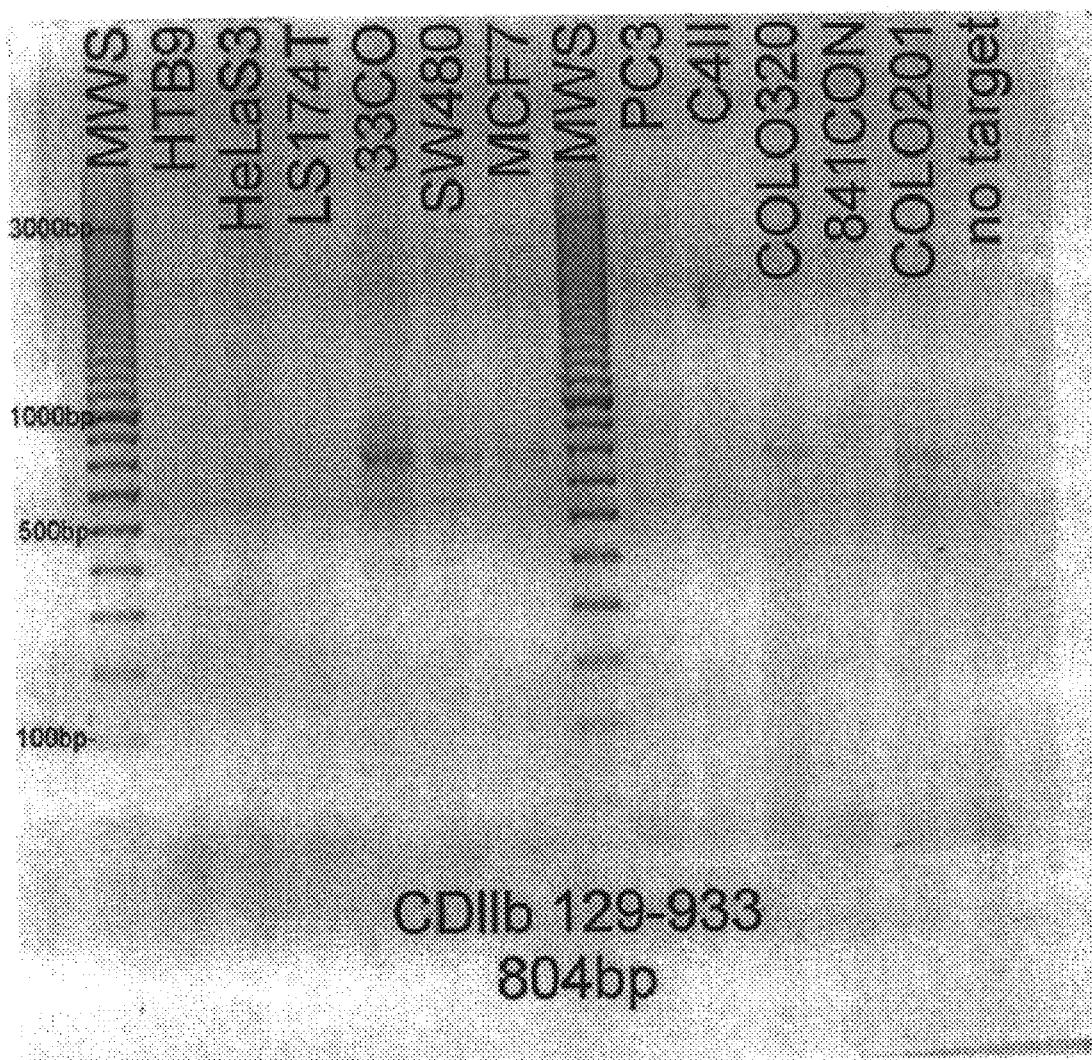
FIG. 12 shows the results of amplification of cDNA for the CD11b chain of CR3 from a variety of human cell lines by the CD11b 129-933 primer set.
Figure 13:
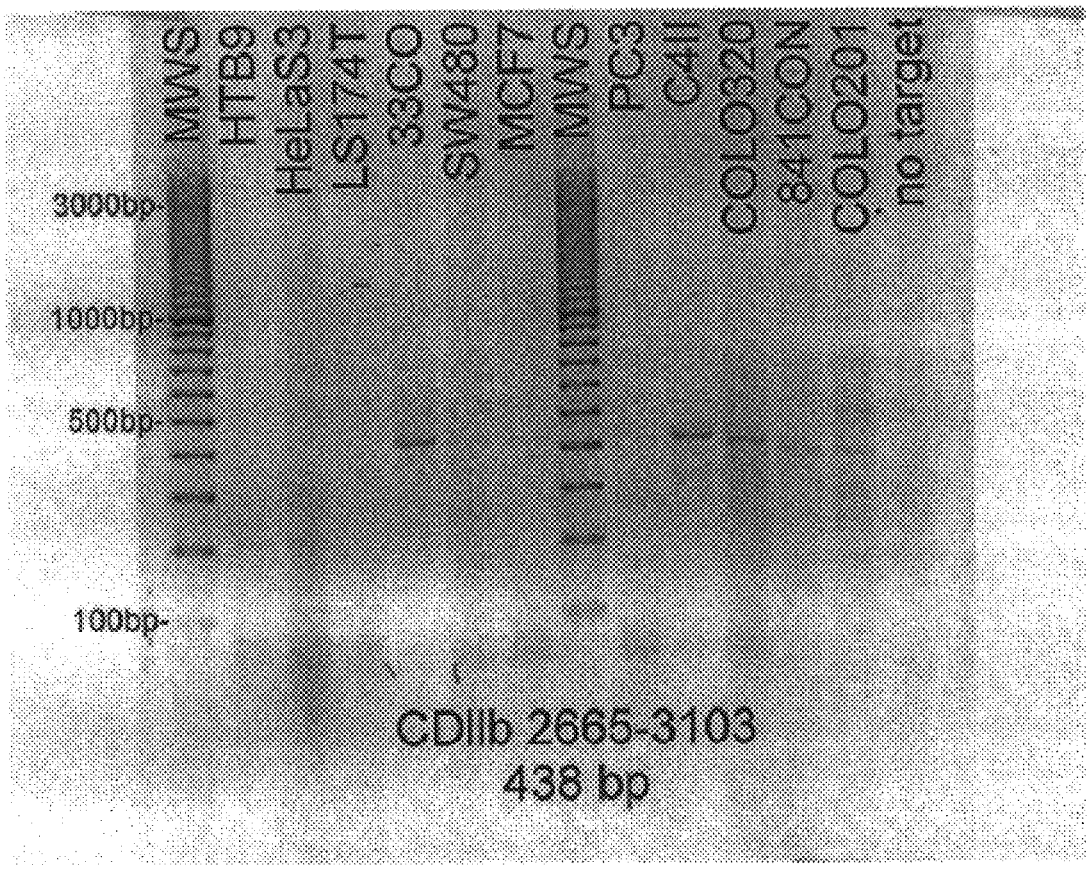
FIG. 13 shows the results of amplification of cDNA for the CD11b chain of CR3 from a variety of human cell lines by the CD11b 2665-3103RT primer set.

Other primer sets from the list shown in Table VI are also useful in detecting CR3/CD11b product. Examples of the cancer cell line surveys are shown in FIGS. 12 and 13 using the primer sets 129-933RT and 2665-3103RT, respectively. The amplification conditions were the same as those described above, with the annealing temperature set at 65° C. for the 129-933 RT primers and at 70° C. for the 2665-3103RT primers. In these figures, the cell lines tested, listed from left to right, beginning with Lane 2, are as follows: Lane 2, HTB9; Lane 3, HeLaS3; Lane 4, LS174T; Lane 5, 33-CO; Lane 6, SW480; Lane 7, MCF-7; Lane 9, PC3; Lane 10, C4ii; Lane 11, COLO320; Lane 12, 841CON; Lane 13, COLO201; Lanes 1 and 8 contain molecular weight standards (in 100 base increments) and Lane 13 shows a control in which target was absent. The survey of cell lines reproduced in these figures show that four of the six colon cell lines possess CR3 mRNA. Of the two colon cell lines which were negative for CR3 MRNA, 841CON is derived from normal colon tissue and LS174T is from a mucin-producing adenocarcinoma. The cervical cancer line HeLaS3 and breast cancer line MCF-7 were also positive for CR3 expression with these two primer sets. The bladder cancer line HTB9, the prostate cancer line PC3, and the cervical cancer line C4ii did not produce levels of CD11b niRNA detectable in these assays.

5 D. Results of RT-PCR of CR3 From Human Normal and Cancerous Colon Tissues

Matching normal and cancerous colon tissues were obtained from surgical specimens and were tested for the expression of CR3. Surgical material was stored frozen at −80° C. until use.

1. Preparation of total tissue RNA was performed as follows. The tissue, while still frozen, was minced with a surgical scissors and then transferred to a Potter-Elvejehm tissue grinder (Kontes, Vineland, N.J.) in an ice bath. Preparation of MRNA was facilitated by the addition of 5 mL (per each approximately one cubic centimeter of tissue) of a Lysis Buffer containing: 7.5 M Guanidine HCl, 25 mM TES, 10 mM EDTA, 0.05% Taurodeoxycholate, 1 mM 2-mercaptoethanol, pH 7.5 (all reagents Molecular Biology Grade from Sigma). The tissue was then homogenized by multiple passes in the tissue grinder with a tight-fitting pestle, while immersed in ice. The lysate was extracted with equal volumes of phenol and chloroform/isoamyl alcohol. The aqueous phase was aspirated and re-extracted with an equal volume of chloroform/isoamyl alcohol. The aqueous phase was then precipitated with $\frac{1}{10}$ volume of 3M sodium acetate (Cat #16-019B, BioWhittaker, Walkersville, Md.) and one volume of isopropanol (Sigma, Molecular Biology Grade). The RNA pellet obtained after centrifugation at 10,000×G for 30 minutes was washed one time with 70% isopropanol before being redissolved in Molecular Biology Grade water for further use.

Figure 14:
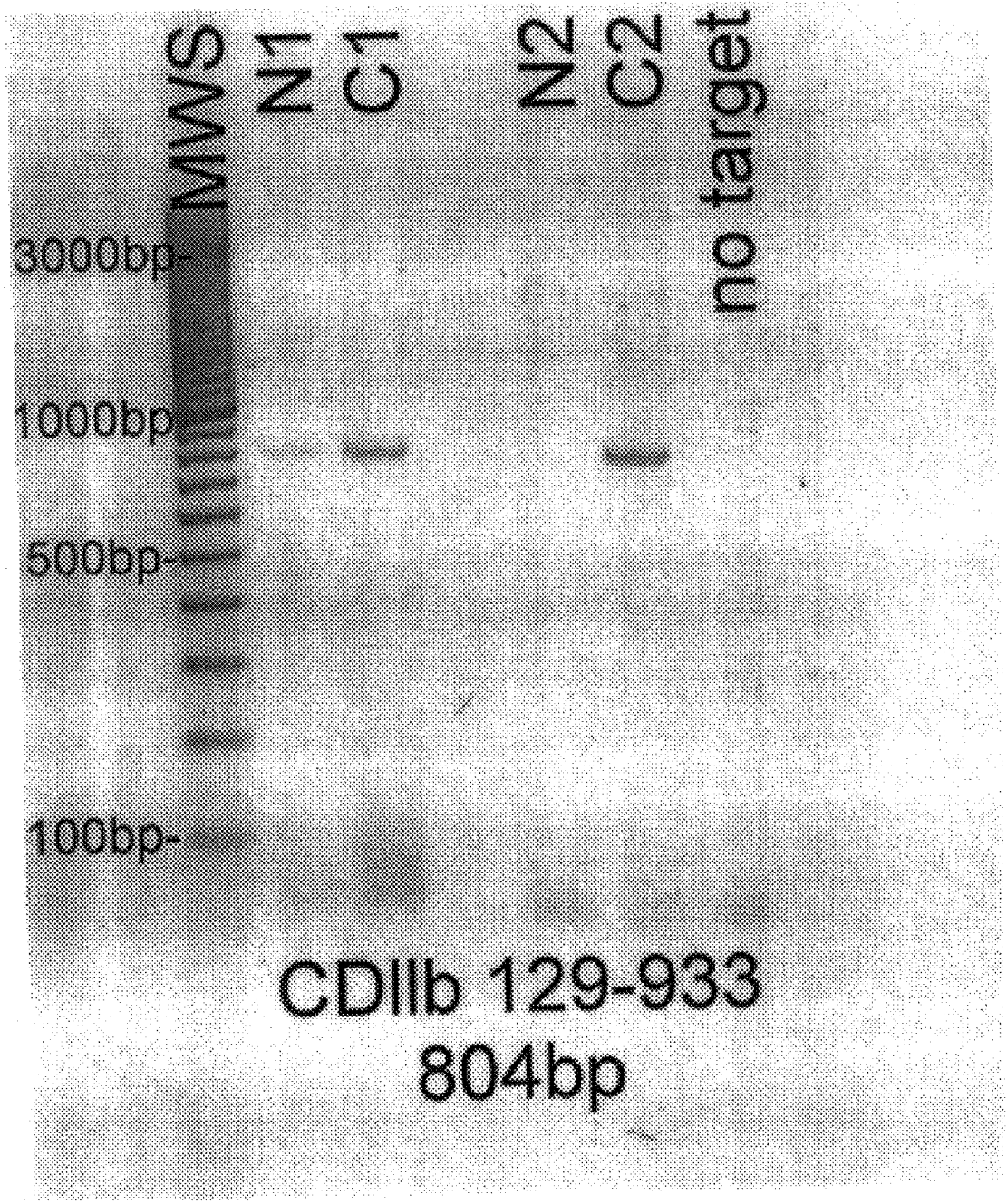
FIG. 14 shows the results of amplification of cDNA for the CD11b chain of CR3 from matched normal (N1 and N2) and cancerous (C1 and C2) colon tissue from two patients with colon cancer, using the CD11b 129-933RT primer set. The lane labeled MWS contains molecular weight markers.
Figure 15:
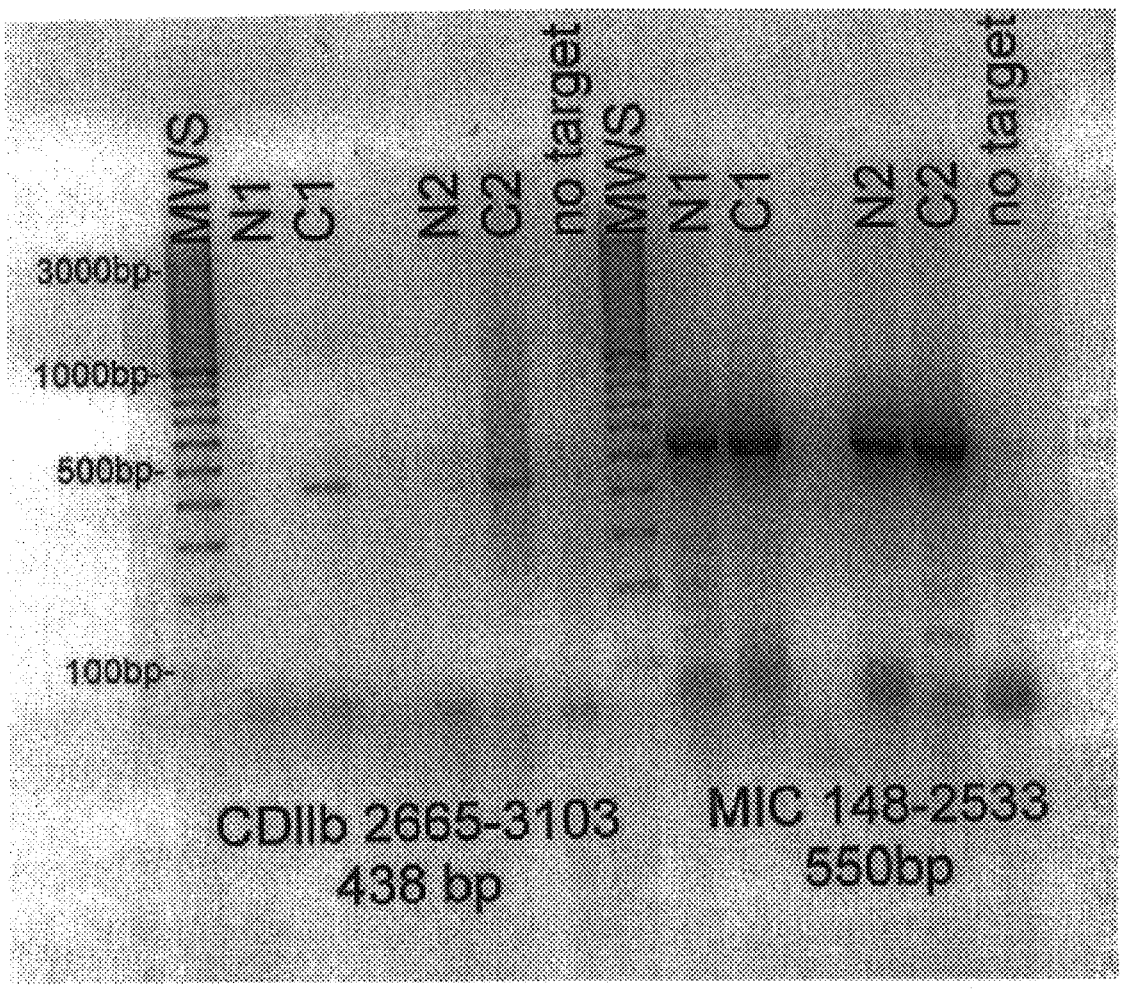
FIG. 15 shows, on the left half of the figure, the results of amplification of cDNA for the CD11b chain of CR3 from matched normal (N1 and N2) and cancerous (C1 and C2) colon tissue from two patients with colon cancer, using the CD11b 2665-3103RT primer set. Amplification of cDNA from the same specimens with the MIC 148-2533RT control primer set is shown in the right half of the figure. Two lanes labeled MWS contain molecular weight markers.

2. RT-PCR was performed with primer sets 129-933RT and 2665-3103RT, as described above. Equal quantities of RNA from the normal tissue or the cancerous tissue were loaded into the reaction mixtures. FIG. 14 shows the results for amplification of normal colon specimen 1 (N1, Lane 2), matched colon cancer specimen 1 (C1, Lane 3), normal colon specimen 2 (N2, Lane 5) and colon cancer specimen 2 (C2, Lane 6) with the 129-933RT primer set. In this figure, Lane 1 contains molecular weight standards, Lane 4 is blank, and Lane 7 contains a control with no target. FIG. 15 shows the same specimens amplified with the 2665-3103RT primer set on the left half of the gel. FIG. 15 also shows the amplification of a control sequence, β2-microglobulin (MIC), on the right half of the gel, amplified according to the protocol and with primers specified in Corey, E., et al. (*Clinical Chemistry* 43:443–452, 1997). In FIG. 15, the samples are (beginning from the left) as follows: Lanes 1 and 8, molecular weight markers; Lanes 2 and 9, N1; Lanes 3 and 10, C1; Lanes 4 and 11, blank; Lanes 5 and 12, N2; Lanes 6 and 13, C2; Lanes 7 and 14, no target. The amplification of the MIC target demonstrates that the quantity and quality of total RNA containing the CD11b target mRNA was comparable for both normal and cancerous tissues for both specimens tested. The results of the two CD11b primer amplifications clearly show an upregulation of CR3 in the colon cancer specimens.

Figure 16:
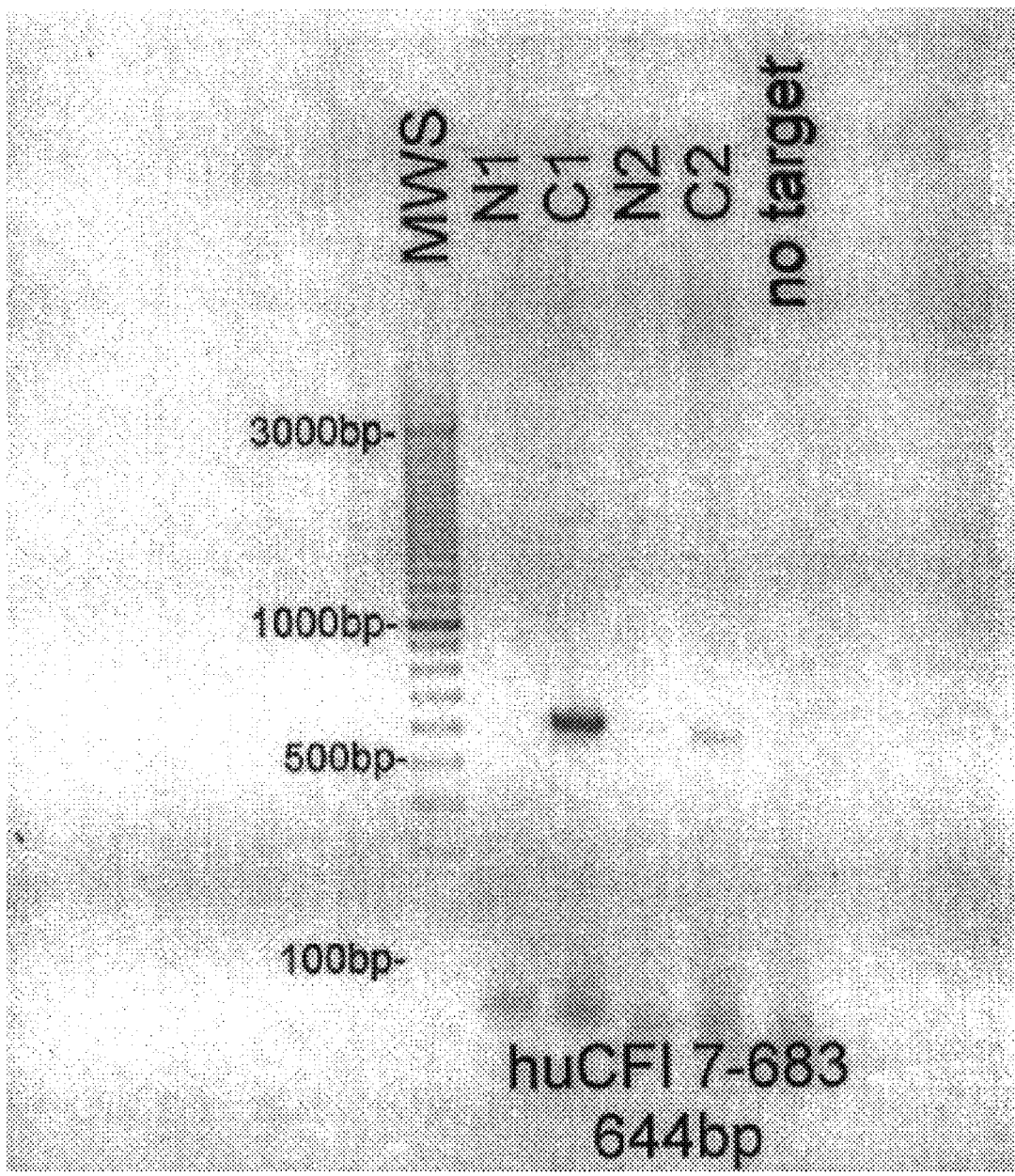
FIG. 16 shows the results of amplification of cDNA for complement Factor I from matched normal (N1 and N2) and cancerous (C1 and C2) colon tissue from two patients with colon cancer, using the CFI primer set FI7us and FIG683ds.

3. RT-PCR was also performed with the CFI primer pair FI7us and FIG683ds described above in Example IV, FI7us and FIG683ds, each used at 0.50 nmoles per 100 μL reaction mixture. Annealing conditions were 62° C. for 30 seconds and extension was at 72° C. for 90 seconds, with 40 cycles. Positive results, defined to be the identification of a 472-base pair amplicon, were determined by electrophoresis as described above. When the matched normal and cancerous colon tissues from patients 1 and 2 in the CD11b study were examined, as shown in FIG. 16, complement Factor I MRNA expression was clearly upregulated in the tumors. The samples on the gel (beginning from the left) are as follows: Lane 1, molecular weight markers; Lane 2, N1; Lane 3, C1; Lane 4, N2; Lane 5, C2; Lane 6, no target. The result, as shown in this figure, is unexpected and significant since Factor I has not previously been described as being expressed in colon tumors, and since Factor I with Factor H as a cofactor is capable of hydrolyzing C3b, resulting in failure of the Membrane Attack Complex (MAC) to assemble on the cell surface. This in turn would enable a colon cancer cells to evade lysis by the immune system.

All publications and patent applications mentioned in this specification are herein incorporated by reference to the same extent as if each individual publication or patent application was specifically and individually incorporated by reference.

From the foregoing it will be appreciated that, although specific embodiments of the invention have been described herein for purposes of illustration, various modifications may be made without deviating from the spirit and scope of the invention.

What is claimed is:

1. A method of screening for colorectal cancer comprising testing a sample from a warm-blooded animal for the presence of complement Factor I (CFI) protein or a CFI related protein which has at least 50% amino acid sequence identity with CFI protein, an RNA encoding CFI protein or CFI related proteins or the cDNA thereof, whereby detection of said presence is indicative of colorectal cancer in the animal.

2. The method of claim 1 wherein the molecule detected is CFI proteins an RNA encoding CFI protein or the cDNA thereof.

3. The method of claim 1 wherein the molecule detected is CFI related proteins an RNA encoding CFI related proteins or the cDNA thereof, wherein the CFI related protein has at least 85% amino acid sequence identity with CFI protein.

4. The method of any one of claims 1, 2 or 3, wherein the warm-blooded animal is a human.

* * * * *

UNITED STATES PATENT AND TRADEMARK OFFICE
CERTIFICATE OF CORRECTION

PATENT NO. : 6,221,621 B1
DATED : April 24, 2001
INVENTOR(S) : Robert J. Kinders et al.

Page 1 of 1

It is certified that error appears in the above-identified patent and that said Letters Patent is hereby corrected as shown below:

<u>Column 35, claim 1,</u>
Lines 39 and 40, "or a CFI. related protein" should read -- or a CFI related protein --.
Line 42, "related proteins or the cDNA" should read -- related protein, or the cDNA --.

<u>Column 35, claim 2,</u>
Line 46, "CFI proteins an RNA" should read -- CFI protein, an RNA --.

<u>Column 36, claim 3,</u>
Line 37, "related proteins an RNA" should read -- related protein, and RNA --.
Lines 47 and 48, "related proteins or" should read -- related protein, or --.

Signed and Sealed this

Twenty-ninth Day of January, 2002

Attest:

*Attesting Officer*

JAMES E. ROGAN
*Director of the United States Patent and Trademark Office*

SEQUENCE LISTING

```
<160> NUMBER OF SEQ ID NOS: 15

<210> SEQ ID NO 1
<211> LENGTH: 22
<212> TYPE: DNA
<213> ORGANISM: Artificial Sequence
<220> FEATURE:
<223> OTHER INFORMATION: Primer for PCR amplification of DAF mRNA

<400> SEQUENCE: 1
atgatgaagg agagtggagt gg                                              22

<210> SEQ ID NO 2
<211> LENGTH: 22
<212> TYPE: DNA
<213> ORGANISM: Artificial Sequence
<220> FEATURE:
<223> OTHER INFORMATION: Primer for PCR amplification of DAF mRNA

<400> SEQUENCE: 2
ctccttgctc tgttgacatt cc                                              22

<210> SEQ ID NO 3
<211> LENGTH: 27
<212> TYPE: DNA
<213> ORGANISM: Artificial Sequence
<220> FEATURE:
<223> OTHER INFORMATION: Primer for PCR amplification of CFI mRNA

<400> SEQUENCE: 3
gcaaggtcac ttatacatct caagagc                                         27

<210> SEQ ID NO 4
<211> LENGTH: 28
<212> TYPE: DNA
<213> ORGANISM: Artificial Sequence
<220> FEATURE:
<223> OTHER INFORMATION: Primer for PCR amplification of CFI mRNA

<400> SEQUENCE: 4
cccattcaca cactgaaaga agtcatcc                                        28

<210> SEQ ID NO 5
<211> LENGTH: 21
<212> TYPE: DNA
<213> ORGANISM: Artificial Sequence
<220> FEATURE:
<223> OTHER INFORMATION: Primer for PCR amplification of CR3 mRNA

<400> SEQUENCE: 5
tcagtggtgc ctgcaacccc t                                               21

<210> SEQ ID NO 6
<211> LENGTH: 21
```

```
<212> TYPE: DNA
<213> ORGANISM: Artificial Sequence
<220> FEATURE:
<223> OTHER INFORMATION: Primer for PCR amplification of CR3 mRNA

<400> SEQUENCE: 6
ttggacactg aaaacgcaat g                                              21

<210> SEQ ID NO 7
<211> LENGTH: 21
<212> TYPE: DNA
<213> ORGANISM: Artificial Sequence
<220> FEATURE:
<223> OTHER INFORMATION: Primer for PCR amplification of CR3 mRNA

<400> SEQUENCE: 7
cccaatgacg tagcgaatga c                                              21

<210> SEQ ID NO 8
<211> LENGTH: 21
<212> TYPE: DNA
<213> ORGANISM: Artificial Sequence
<220> FEATURE:
<223> OTHER INFORMATION: Primer for PCR amplification of CR3 mRNA

<400> SEQUENCE: 8
tacgtcattg gggtgggaga t                                              21

<210> SEQ ID NO 9
<211> LENGTH: 20
<212> TYPE: DNA
<213> ORGANISM: Artificial Sequence
<220> FEATURE:
<223> OTHER INFORMATION: Primer for PCR amplification of CR3 mRNA

<400> SEQUENCE: 9
ctgctatccg ctggctatgg                                                20

<210> SEQ ID NO 10
<211> LENGTH: 20
<212> TYPE: DNA
<213> ORGANISM: Artificial Sequence
<220> FEATURE:
<223> OTHER INFORMATION: Primer for PCR amplification of CR3 mRNA

<400> SEQUENCE: 10
ggggacgtaa atggggacaa                                                20

<210> SEQ ID NO 11
<211> LENGTH: 21
<212> TYPE: DNA
<213> ORGANISM: Artificial Sequence
<220> FEATURE:
<223> OTHER INFORMATION: Primer for PCR amplification of CR3 mRNA

<400> SEQUENCE: 11
cgctggttct ggagtgtcga c                                              21

<210> SEQ ID NO 12
<211> LENGTH: 21
<212> TYPE: DNA
<213> ORGANISM: Artificial Sequence
<220> FEATURE:
<223> OTHER INFORMATION: Primer for PCR amplification of CR3 mRNA

<400> SEQUENCE: 12
```

```
caaggaagcc ggagaggtca g                                              21

<210> SEQ ID NO 13
<211> LENGTH: 21
<212> TYPE: DNA
<213> ORGANISM: Artificial Sequence
<220> FEATURE:
<223> OTHER INFORMATION: Primer for PCR amplification of CR3 mRNA

<400> SEQUENCE: 13
agtcggactg agagggcaag c                                              21

<210> SEQ ID NO 14
<211> LENGTH: 21
<212> TYPE: DNA
<213> ORGANISM: Artificial Sequence
<220> FEATURE:
<223> OTHER INFORMATION: Primer for PCR amplification of CR3 mRNA

<400> SEQUENCE: 14
gcagcataaa ccaccccatc t                                              21

<210> SEQ ID NO 15
<211> LENGTH: 20
<212> TYPE: DNA
<213> ORGANISM: Artificial Sequence
<220> FEATURE:
<223> OTHER INFORMATION: Primer for PCR amplification of CR3 mRNA

<400> SEQUENCE: 15
aggcagctct gtcgggaagg                                                20
```